United States Patent
Gellman et al.

(10) Patent No.: US 8,269,039 B2
(45) Date of Patent: Sep. 18, 2012

(54) AMINO ACIDS AND CATALYTIC PREPARATORY METHODS

(75) Inventors: Samuel Helmer Gellman, Madison, WI (US); Yonggui Chi, Berkeley, CA (US); Li Guo, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 586 days.

(21) Appl. No.: 12/383,370

(22) Filed: Mar. 23, 2009

(65) Prior Publication Data
US 2009/0264676 A1 Oct. 22, 2009

Related U.S. Application Data

(60) Provisional application No. 61/070,298, filed on Mar. 21, 2008.

(51) Int. Cl.
*C07C 205/51* (2006.01)
*C07C 205/44* (2006.01)
(52) U.S. Cl. ........ 562/571; 562/553; 562/434; 568/423; 568/704
(58) Field of Classification Search .................. None
See application file for complete search history.

(56) References Cited

U.S. PATENT DOCUMENTS 3,024,232 A * 3/1962 Hodge ............................ 544/63

OTHER PUBLICATIONS

Hayashi et al. (Angewandte Chemie International Edition, Jul. 2005, vol. 44, Issue 27, pp. 4212-4215).*
Warner et al. (Journal of the American Chemical Society, 1952, vol. 74, pp. 1064-1066).*
Chi, Y., et al., "Practical synthesis of enantiomerically pure beta2-amino acids via proline-catalyzed diastereoselective aminomethylation of aldehydes.", *J Am Chem Soc.*, 129(18), (May 9, 2007), 6050-5.
Chi, Yonggui, et al., "Enantioselective organocatalytic aminomethylation of aldehydes: a role for ionic interactions and efficient access to beta2-amino acids.", *J Am Chem Soc.*, 128(21), (May 31, 2006), 6804-5.
Chi, Yonggui, "The development and application of asymmetric organocatalytic Michael reactions and Mannich reactions", *PhD Thesis, University of Wisconsin-Madison*, (2007), 370 pgs.
Corse, J., et al., "Dihydrozeatin: An improved synthesis and resolution of both isomers", *Journal of Plant Growth Regulation*, vol. 2, Issue 1, (1983), 47-57.
Gilbert, B. C., et al., "Electron Spin Resonance Studies. Part XXXIV. The Use of the aci-Anion from Nitromethane as a Spin Trap for Organic Radicals in Aqueous Solution", *Journal of the Chemical Society—Perkin Transactions II*, (1972), 1272-1279.
Wiesner, M., et al., "Tripeptides as efficient asymmetric catalysts for 1,4-addition reactions of aldehydes to nitroolefins—a rational approach.", *Angew Chem Int Ed Engl.*, 47(10), (2008), 1871-4.

* cited by examiner

*Primary Examiner* — Rosalynd Keys
(74) *Attorney, Agent, or Firm* — Clise, Billion & Cyr, P.A.; Michael H. Haukaas

(57) ABSTRACT

The invention provides novel compounds and methods to carry out organocatalytic Michael additions of aldehydes to nitroethylene catalyzed by a proline derivative to provide α-substituted-γ-nitroaldehydes. The reaction can be rendered enantioselective when a chiral pyrrolidine catalyst is used, allowing for Michael adducts in nearly optically pure form (e.g., 96-99% e.e.). The Michael adducts can bear a single substituent or dual substituents adjacent to the carbonyl. The Michael adducts can be efficiently converted to protected $\gamma^2$-amino acids, which are essential for systematic conformational studies of γ-peptide foldamers.

22 Claims, No Drawings

AMINO ACIDS AND CATALYTIC PREPARATORY METHODS

RELATED APPLICATIONS

This application claims priority under 35 U.S.C. §119(e) to U.S. Provisional Patent Application No. 61/070,298, filed Mar. 21, 2008, which is incorporated herein by reference.

GOVERNMENT SUPPORT

This invention was made with government support under Grant Numbers CHE-0140621 and CHE-055190 awarded by the National Science Foundation, and Grant Number GM56414 awarded by the National Institutes of Health. The United States Government has certain rights in the invention.

BACKGROUND OF THE INVENTION

The development of asymmetric conjugate addition reactions for carbon-carbon bond formation remains an important challenge in organic synthesis.[1,2] Much recent work has focused on organocatalytic Michael addition of carbonyl compounds to nitroalkenes.[3-5] Among these reactions, Michael addition of aldehydes to nitroalkenes is of particular interest because of the valuable synthetic intermediates that are generated.[4] β-Aryl nitroalkenes have been the most common Michael acceptors. These Michael reactions provide α,β-disubstituted-γ-nitrobutyl aldehydes. Access to adducts that bear only a single substituent adjacent to a carbonyl are of interest because they can be readily converted to $\gamma^2$-amino acids. $\gamma^2$-Amino acids represent potential building blocks for γ-peptide[6] and heterogeneous backbone foldamers.[7] Derivatives of the neurotransmitter γ-amino butyric acid (GABA)[8] are of potential biomedical utility, illustrated by the use of Pregabalin and Baclofen to treat neurological disorders.[9]

Preparation of enantiomerically pure γ-amino acids is challenging and this synthetic hurdle has limited the study of γ-peptide foldamers to date. A variety of routes to enantioenriched $\gamma^2$-amino acids have been described,[10] but these approaches often involve specialized chiral auxiliaries and may not be ideal for preparing multigram quantities of protected $\gamma^2$-amino acids bearing diverse side chain functionality, which is necessary for foldamer research.

Accordingly, new methods for the synthesis of $\gamma^2$-amino acids, especially enantioselective methods, would significantly aid the preparation and study of γ-peptide and heterogeneous backbone foldamers. Such methods would also help to facilitate evaluation of their potential biomedical uses. Therefore, new synthetic methods for the preparation of versatile adducts that can be converted to converted to $\gamma^2$-amino acids would be of significant value to the research community.

SUMMARY

The invention provides a compound of formula I:

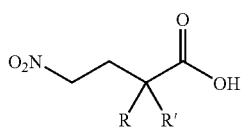

(I)

wherein R is hydrogen, alkyl, cycloalkyl, aryl, heteroaryl, or heterocycle; R' is alkyl, cycloalkyl, aryl, heteroaryl, or heterocycle; and the alkyl, cycloalkyl, aryl, heteroaryl, or heterocycle is optionally substituted with one to five substituents, for example, alkyl, alkoxy, halo, hydroxy, aryl, heteroaryl, heterocycle, cycloalkyl, alkanoyl, alkoxycarbonyl, amino, alkylamino, dialkylamino, acylamino, nitro, trifluoromethyl, trifluoromethoxy, carboxy, carboxyalkyl, keto, arylsulfonyl, cyano, or azide groups, or a substituent as described herein for the definition of substituents; or a salt thereof. In some embodiments, one or both of R and R' are not methyl or butyl, for example, n-butyl. The compound can be enantiomerically enriched and can be in an (R) or (S) configuration. For example, the compound can have an enantiomeric purity of greater than about 90%, about 95%, or about 98%.

The invention also provides a compound of formula II:

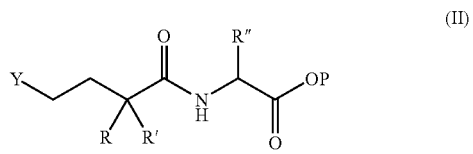

(II)

wherein R and R' are each independently hydrogen, alkyl, cycloalkyl, aryl, heteroaryl, or heterocycle; R" is an amino acid side chain; P is hydrogen or a carboxylic acid protecting group; Y is nitro, amino, or protected amino; and the alkyl, cycloalkyl, aryl, heteroaryl, or heterocycle is optionally substituted with one to five substituent groups, as described above for formula I. In some embodiments, one of R and R' is not methyl or butyl, for example, n-butyl. In other embodiments, R and R' are not both methyl.

For example, the compound of formula II can be an α-amino acid linked to a compound of formula I through an amide bond. The α-amino acid can be protected at its carboxylic acid. The amino acid side chain can be any side chain of any known α-amino acid, for example, the a side chain of any of the twenty naturally occurring amino acids in humans, including a hydrogen of proline. In one embodiment, R is hydrogen, R' is ethyl, R" is benzyl, P is methyl or acetyl, and Y is nitro or Boc-protected amino. The compound can have an enantiomeric purity of greater than about 95% with respect to the carbon attached to R. Diastereomerically pure compounds of formula II can be provided by using enantiomerically pure α-amino acids in their preparation.

The invention further provides highly efficient Michael reactions between the highly reactive nitroethylene (A) and aldehydes (B) to provide the Michael products C, α-substituted-γ-nitrobutyl aldehydes (Scheme 1).

Scheme 1.

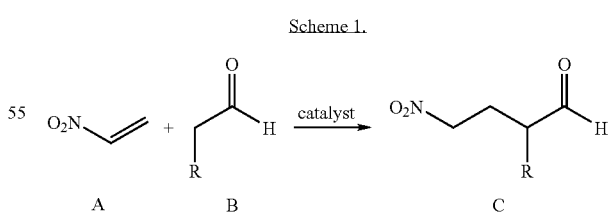

The use of a chiral pyrrolidine catalyst allows for the highly enantioselective preparation of Michael products. The reaction requires only very low catalyst loading (e.g., about 1-2 mol %) when carried out in the presence of certain acids as cocatalysts, and high yields are readily achieved. The substituent R can be any organic group or functional group that is tolerant of the mild Michael reaction conditions.

The Michael products (C) are valuable building blocks for organic synthesis. For example, α-substituted-γ-nitroaldehyde C can be converted to γ²-amino acids F (α-substituted-γ-aminobutyric acids) and their derivatives (e.g., β-substituted-δ-nitrobutyl alcohols D, β-substituted-δ-aminobutyl alcohols E, and γ-lactams G, etc.) (Scheme 2). The products can be broadly used from basic research (e.g. foldamer research, etc.) to product development (e.g., pharmaceutically relevant molecules).

Scheme 2.

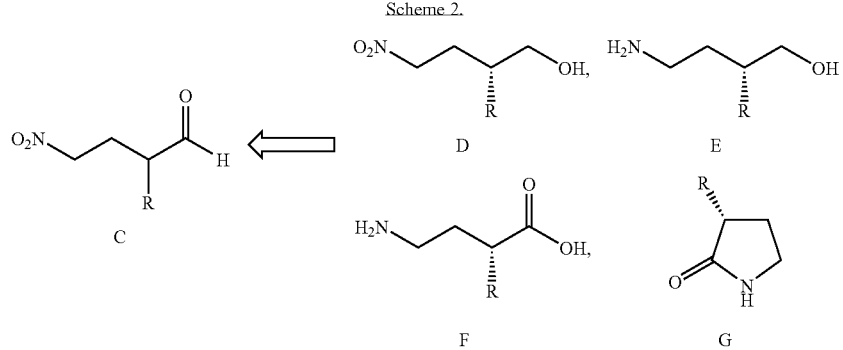

Accordingly, the invention provides a method for preparing an α-substituted-γ-nitrobutyraldehyde comprising contacting nitroethylene and an aldehyde in the presence of an organic solvent, a proline derivative, and optionally a carboxylic acid, under suitable reaction conditions so as to provide the α-substituted-γ-nitrobutyraldehyde.

The invention also provides a method for preparing an α-substituted-γ-nitrobutyraldehyde comprising contacting nitroethylene and an aldehyde under suitable reaction conditions to provide the product, for example, in the presence of an organic solvent, an (S)- or (R)-diphenylprolinol trialkyl silyl ether, and optionally a nitrobenzoic acid, for a period of time sufficient to provide the α-substituted-γ-nitrobutyraldehyde, wherein the α-substituted-γ-nitrobutyraldehyde is prepared in at least about 80%, 90%, 95%, or 98% enantiomeric purity.

The invention further provides a method for preparing a compound of formula III:

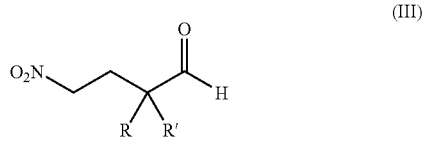

(III)

wherein R and R' are each independently hydrogen or optionally substituted alkyl, cycloalkyl, aryl, heteroaryl, or heterocycle;

comprising contacting a compound of formula IV:

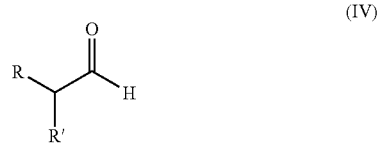

(IV)

wherein R is as defined for formula III, and nitroethylene in the presence of an organic solvent, a proline derivative, and optionally a carboxylic acid, for a period of time sufficient to provide the compound of formula III. The compound of formula III can be enantiomerically enriched or substantially enantiomerically pure, with respect to the carbon attached to R, for example, when the proline derivative is a chiral pyrrolidine catalyst.

In another embodiment, the invention provides a method for preparing an enantiomerically pure α-substituted-γ-amino acid comprising contacting nitroethylene and an aldehyde in the presence of an organic solvent, an (S)- or (R)-diphenylprolinol trialkyl silyl ether, and optionally a carboxylic acid, for a period of time sufficient to provide an α-substituted-γ-nitrobutyraldehyde. The aldehyde of the α-substituted-γ-nitroaldehyde can be reduced to an alcohol and the alcohol can be oxidized to a carboxylic acid. A peptide bond can optionally be formed with the carboxylic acid and the nitrogen moiety of an amino acid that has a protected carboxylic acid group. The nitro moiety of the α-substituted-γ-nitrobutyraldehyde can be reduced to an amine, to provide the enantiomerically pure α-substituted-γ-amino acid, or an amide derivative thereof. The method can further include protecting the amine group of the α-substituted-γ-amino acid with a nitrogen protecting group, for example, a Boc group.

The invention also provides a method to formally aminoethylate an aldehyde, and a concise synthesis of γ²-amino acids and their derivatives via novel, highly efficient and selective organocatalytic Michael additions of aldehydes to nitroethylene. Additionally, the invention provides a method to prepare an amide compound comprised of an α-substituted-γ-amino acid coupled to an α-amino acid directly from an α-substituted-γ-nitrobutyraldehyde.

DETAILED DESCRIPTION

Currently, γ²-amino acids are an important class of non-natural amino acids that are very difficult and/or expensive to prepare. Literature methods for making γ²-amino acids are very inefficient, and not very useful for scalable synthesis or structural diversity. These methods typically require about six synthetic steps, harsh conditions, limited functional group tolerance, low overall yields, and the separation of diasteriomers, which further reduces the synthetic efficiency of such methods.

The methods described herein allow for the preparation of γ²-amino acids with fewer steps than known methods. The Michael addition reaction is highly enantioselective and high overall isolated yields are achieved. Only a minimal use of chromatography is typically used for product purification, and the methods are amenable to large scale synthesis. The reaction conditions are mild, and are thus tolerant of a diverse range of functional groups. The starting materials, including the catalyst, are typically readily available and inexpensive. Accordingly, the invention provides flexible and efficient catalytic methods for amino aldehyde and $\gamma^2$-amino acid synthesis. The methods can provide either the (R)- or (S)-enantiomer of the Michael adduct.

DEFINITIONS

As used herein, certain terms have the following meanings. All other terms and phrases used in this specification have their ordinary meanings as one of skill would understand. Such ordinary meanings may be obtained by reference to technical dictionaries, such as *Hawley's Condensed Chemical Dictionary* $14^{th}$ Edition, by R. J. Lewis, John Wiley & Sons, New York, N.Y., 2001.

The term "and/or" means any one of the items, any combination of the items, or all of the items with which this term is associated.

The singular forms "a," "an," and "the" include plural reference unless the context clearly dictates otherwise. Thus, for example, a reference to "a compound" includes a plurality of such compounds, so that a compound X includes a plurality of compounds X.

The term "about" can refer to a variation of ±5%, 10%, or 20% of the value specified. For example, "about 50" percent can in some embodiments carry a variation from 45 to 55 percent. For integer ranges, the term "about" can include one or two integers greater than and less than a recited integer.

The term "contacting" refers to the act of touching, making contact, or of bringing to immediate or close proximity, including at the molecular level, for example, to allow two suitable compounds to chemically react with each other.

The term "α-substituted-γ-nitrobutyraldehyde" refers to a compound of the formula $O_2N$—$CH_2$—$CH_2$—$CH(R)$—CHO, wherein the substituent R is considered to be 'alpha' to the aldehyde moiety. The group R can be any organic group or functional group, such as an optionally substituted alkyl group, an optionally protected amino acid or derivative thereof, and/or a substituent as described herein. The term α-substituted-γ-nitrobutyraldehyde can also refer to a compound of the formula $O_2N$—$CH_2$—$CH_2$—$C(R)(R)$—CHO, wherein the compound has two substituents 'alpha' to the aldehyde moiety.

The aldehydes useful for the reactions described herein have at least one α-hydrogen atom. Accordingly, the aldehydes employed with have either an α-methylene group or an α-methine group. An "aldehyde that has an α-methylene group" refers to a compound that includes a moiety of the formula —$CH_2$—CHO, and an "aldehyde that has an α-methine group" refers to a compound that includes a moiety of the formula >CH—CHO.

The term "proline derivative" refers to L-proline, R-proline, or a derivative thereof. Such derivatives include various pyrrolidine compounds, including certain chiral pyrrolidine catalyst known in the art. Examples of proline derivatives include diarylprolinol trialkyl silyl ethers, such as diphenylprolinol trialkyl silyl ether, for example, diphenylprolinol trimethyl silyl ether. A proline derivative can be racemic, scalemic, or the derivative can be the (R) or (S) enantiomer.

The term "solvent" refers to any liquid that can dissolve a compound to form a solution. Solvents include water and various organic solvents, such as hydrocarbon solvents, for example, alkanes and aryl solvents. Examples include hexanes, DMF, DMA, DMSO, benzene, toluene, xylenes, and alcoholic solvents such as methanol, ethanol, propanol, isopropanol, and linear or branched (sec or tert) butanol.

A "reducing agent" can effectuate the removal of oxygen from a compound or the addition of hydrogen to a compound. Typical reducing agents include various hydride reagents, such as borohydride reagents and aluminum hydride reagents, for example, sodium borohydride and lithium aluminum hydride.

An "oxidizing agent" can effectuate the addition of oxygen to a compound or the removal of hydrogen from a compound. Typical reducing agents include various metal oxides and metal catalysts (e.g., a transition metal, optionally adsorbed onto carbon) in the presence of hydrogen gas. Examples include chromium oxides such as the Jones reagent, and palladium on carbon in the presence of hydrogen gas.

The term "enantiomerically enriched" refers to mixtures that have one enantiomer present to a greater extent than another. In one embodiment, the term "enantiomerically enriched" refers to a mixture having at least about 50% enantiomeric excess ("ee"); in another embodiment, the term refers to a mixture having at least about 75% ee; in another embodiment, the term refers to a mixture having at least about 80%; in another embodiment, the term refers to a mixture having at least about 85%; in another embodiment, the term refers to a mixture having at least about 90%; in another embodiment, the term refers to a mixture having at least about 92%; in another embodiment, the term refers to a mixture having at least about 95%; in another embodiment, the term refers to a mixture having at least about 98%; and in another embodiment, the term "enantiomerically enriched" refers to a mixture having at least about 99% ee.

The term "enantiomerically enriched" includes enantiomerically pure mixtures, which are mixtures that are substantially free of the species of the opposite optical activity or one enantiomer is present in very low quantities, for example, about 0.01%, about 0.001% or about 0.0001%.

Specific values listed below for radicals, substituents, and ranges, are for illustration only; they do not exclude other defined values or other values within defined ranges for the radicals and substituents.

The term "alkyl" refers to a branched, unbranched, or cyclic carbon chain having, for example, about 1-20 carbon atoms, and often 1-12, 1-10, 1-8, 1-6, or 1-4 carbons. Examples include, but are not limited to, methyl, ethyl, 1-propyl, 2-propyl, 1-butyl, 2-methyl-1-propyl, 2-butyl, 2-methyl-2-propyl(t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted. The alkyl can also be optionally partially or fully unsaturated. As such, the recitation of an alkyl group includes both alkenyl and alkynyl groups. The alkyl can be a monovalent hydrocarbon radical, as described and exemplified above, or it can be a divalent hydrocarbon radical (i.e., an alkylene). In some embodiments, certain alkyl groups can be excluded from a definition. For example, in some embodiments, methyl, ethyl, propyl, butyl, or a combination thereof, can be excluded from a specific definition of alkyl.

The term "cycloalkyl" refers to cyclic alkyl groups of, for example, from 3 to 10 carbon atoms having a single cyclic ring or multiple condensed rings. Cycloalkyl groups include, by way of example, single ring structures such as cyclopropyl, cyclobutyl, cyclopentyl, cyclooctyl, and the like, or multiple ring structures such as adamantyl, and the like. The cycloalkyl can be unsubstituted or substituted. The cycloalkyl group can be monovalent or divalent, and can be optionally substituted as described for alkyl groups. The cycloalkyl group can optionally include one or more cites of unsaturation, for example, the cycloalkyl group can include one or more carbon-carbon double bonds, such as, for example, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and the like.

As used herein, "aryl" refers to an aromatic hydrocarbon group derived from the removal of one hydrogen atom from a single carbon atom of a parent aromatic ring system. The radical attachment site can be at a saturated or unsaturated carbon atom of the parent ring system. The aryl group can have from 6 to 30 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted, as described for alkyl groups.

The term "heteroaryl" refers to a monocyclic, bicyclic, or tricyclic ring system containing one, two, or three aromatic rings and containing at least one nitrogen, oxygen, or sulfur atom in an aromatic ring, and that can be unsubstituted or substituted, for example, with one or more, and in particular one to three, substituents, as described in the definition of "substituted". Typical heteroaryl groups contain 2-20 carbon atoms in addition to the one or more hetoeroatoms. Examples of heteroaryl groups include, but are not limited to, 2H-pyrrolyl, 3H-indolyl, 4H-quinolizinyl, acridinyl, benzo[b]thienyl, benzothiazolyl, β-carbolinyl, carbazolyl, chromenyl, cinnolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl. In one embodiment the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, aryl, or ($C_1$-$C_6$) alkylaryl. In some embodiments, heteroaryl denotes an ortho-fused bicyclic heterocycle of about eight to ten ring atoms derived therefrom, particularly a benz-derivative or one derived by fusing a propylene, trimethylene, or tetramethylene diradical thereto.

The term "heterocycle" refers to a saturated or partially unsaturated ring system, containing at least one heteroatom selected from the group oxygen, nitrogen, silicon, and sulfur, and optionally substituted with one or more groups as defined for the term "substituted". A heterocycle can be a monocyclic, bicyclic, or tricyclic group. A heterocycle group also can contain an oxo group (=O) or a thioxo (=S) group attached to the ring. Non-limiting examples of heterocycle groups include 1,3-dihydrobenzofuran, 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholinyl, piperazinyl, piperidinyl, pyrazolidinyl, pyrazolinyl, pyrrolidine, pyrroline, quinuclidine, tetrahydrofuranyl, and thiomorpholine.

As used herein, the term "substituted" is intended to indicate that one or more (e.g., 1, 2, 3, 4, or 5; in some embodiments 1, 2, or 3; and in other embodiments 1 or 2) hydrogens on the group indicated in the expression using "substituted" is replaced with a "substituent", which can be a selection from the indicated group(s), or with a suitable group known to those of skill in the art, provided that the indicated atom's normal valency is not exceeded, and that the substitution results in a stable compound. Suitable indicated groups include, e.g., alkyl, alkenyl, alkynyl, alkoxy, halo, haloalkyl, hydroxy, hydroxyalkyl, aryl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxyl amine, hydroxyl(alkyl)amine, and cyano. Additionally, the suitable indicated groups can include, e.g., —X, —R, —O⁻, —OR, —SR, —S⁻, —NR$_2$, —NR$_3$, =NR, —CX$_3$, —CN, —OCN, —SCN, —N=C=O, —NCS, —NO, —NO$_2$, =N$_2$, —N$_3$, NC(=O) R, —C(=O)R, —C(=O)NRR—S(=O)$_2$O⁻, —S(=O)$_2$ OH, —S(=O)$_2$R, —OS(=O)$_2$OR, —S(=O)$_2$NR, —S(=O)R, —OP(=O)O$_2$RR, —P(=O)O$_2$RR—P(=O) (O⁻)$_2$, —P(=O)(OH)$_2$, —C(=O)R, —C(=O)X, —C(S)R, —C(O)OR, —C(O)O⁻, —C(S)OR, —C(O)SR, —C(S)SR, —C(O)NRR, —C(S)NRR, —C(NR)NRR, where each X is independently a halogen ("halo"): F, Cl, Br, or I; and each R is independently H, alkyl, aryl, heteroaryl, heterocycle, or a protecting group. As would be readily understood by one skilled in the art, when a substituent is keto (=O) or thioxo (=S), or the like, then two hydrogen atoms on the substituted atom are replaced. In some embodiments, one or more of the substituents above are excluded from the group of potential values for substituents on the substituted group.

As to any of the above groups, which contain one or more substituents, it is understood, of course, that such groups do not contain any substitution or substitution patterns that are sterically impractical and/or synthetically non-feasible. It will be appreciated that the compounds of the invention contain asymmetrically substituted carbon atoms, and may be isolated in optically active or racemic forms. It is well known in the art how to prepare optically active forms, such as by resolution of racemic forms or by synthesis from optically active starting materials. All chiral, diastereomeric, racemic forms and all geometric isomeric forms of a structure are part of this invention.

Any reference to any of the compounds of the invention also includes a salt, hydrate, or solvate thereof. Examples of salts of the compounds of the invention include salts derived from an appropriate base, such as an alkali metal (for example, sodium or potassium), an alkaline earth (for example, calcium or magnesium), ammonium or NX$_4^+$ (wherein X is $C_1$-$C_4$ alkyl). Salts of a hydrogen atom or an amino group include salts of organic carboxylic acids such as acetic, behenic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, sulfuric, phosphoric and sulfamic acids. Salts of a compound of a hydroxy group include the anion of said compound in combination with a suitable cation such as Na⁺ and NX$_4^+$ (wherein X is independently selected from H or a $C_1$-$C_4$ alkyl group).

The term "amino acid" refers to a natural amino acid residue (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acid (e.g. phosphoserine; phosphothreonine; phosphotyrosine; hydroxyproline; gamma-carboxyglutamate; hippuric acid; octahydroindole-2-carboxylic acid; statine; 1,2,3,4,-tetrahydroisoquinoline-3-carboxylic acid; penicillamine; ornithine; citruline; α-methyl-alanine; para-benzoylphenylalanine; phenylglycine; propargylglycine; sarcosine; and tert-butylglycine) residue having one or more open valences. The term also comprises natural and unnatural amino acids bearing amino protecting groups (e.g. acetyl, acyl, trifluoroacetyl, or benzyloxycarbonyl), as well as natural and unnatural amino acids protected at carboxy with protecting groups (e.g. as a $(C_1-C_6)$alkyl, phenyl or benzyl ester or amide). Other suitable amino and carboxy protecting groups are known to those skilled in the art (see for example, T. W. Greene, *Protecting Groups In Organic Synthesis*; Wiley: New York, Third Edition, 1999, and references cited therein; D. Voet, *Biochemistry*, Wiley: New York, 1990; L. Stryer, *Biochemistry*, (3rd Ed.), W.H. Freeman and Co.: New York, 1975; J. March, *Advanced Organic Chemistry, Reactions, Mechanisms and Structure*, (2nd Ed.), McGraw Hill: New York, 1977; F. Carey and R. Sundberg, *Advanced Organic Chemistry, Part B: Reactions and Synthesis*, (2nd Ed.), Plenum: New York, 1977; and references cited therein).

The term "protecting group" refers to a group that, when bound to a hydroxyl, nitrogen, or other heteroatom, prevents undesired reactions from occurring at this group and which can be removed by conventional chemical or enzymatic steps to reestablish the 'unprotected' hydroxyl, nitrogen, or other heteroatom group. The particular removable group employed is often interchangeable with other groups in various synthetic routes. Certain removable protecting groups include conventional substituents such as, for example, allyl, benzyl, acetyl, chloroacetyl, thiobenzyl, benzylidine, phenacyl, methyl methoxy, silyl ethers (e.g., trimethylsilyl (TMS), t-butyl-diphenylsilyl (TBDPS), or t-butyldimethylsilyl (TBS)) and any other group that can be introduced chemically onto a hydroxyl functionality and later selectively removed either by chemical or enzymatic methods in mild conditions compatible with the nature of the product.

A large number of protecting groups and corresponding chemical cleavage reactions are described in *Protective Groups in Organic Synthesis*, Theodora W. Greene (John Wiley & Sons, Inc., New York, 1991, ISBN 0-471-62301-6) ("Greene", which is incorporated herein by reference in its entirety). Greene describes many nitrogen protecting groups, for example, amide-forming groups. In particular, see Chapter 1, Protecting Groups: An Overview, pages 1-20, Chapter 2, Hydroxyl Protecting Groups, pages 21-94, Chapter 4, Carboxyl Protecting Groups, pages 118-154, and Chapter 5, Carbonyl Protecting Groups, pages 155-184. See also Kocienski, Philip J.; *Protecting Groups* (Georg Thieme Verlag Stuttgart, New York, 1994), which is incorporated herein by reference in its entirety. Some specific protecting groups that can be employed in conjunction with the methods of the invention are discussed below.

Typical nitrogen protecting groups described in Greene (pages 14-118) include benzyl ethers, silyl ethers, esters including sulfonic acid esters, carbonates, sulfates, and sulfonates. For example, suitable nitrogen protecting groups include substituted methyl ethers; substituted ethyl ethers; p-chlorophenyl, p-methoxyphenyl, 2,4-dinitrophenyl, benzyl; substituted benzyl ethers (p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2- and 4-picolyl, diphenylmethyl, 5-dibenzosuberyl, triphenylmethyl, p-methoxyphenyl-diphenylmethyl, di(p-methoxyphenyl)phenylmethyl, tri(p-methoxyphenyl)methyl, 1,3-benzodithiolan-2-yl, benzisothiazolyl S,S-dioxido); silyl ethers (silyloxy groups) (trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl, t-butylmethoxy-phenylsilyl); esters (formate, benzoylformate, acetate, choroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), pivaloate, adamantoate, crotonate, 4-methoxycrotonate, benzoate, p-phenylbenzoate, 2,4,6-trimethylbenzoate (mesitoate)); carbonates (methyl, 9-fluorenylmethyl, ethyl, 2,2,2-trichloroethyl, 2-(trimethylsilyl)ethyl, 2-(phenylsulfonyl)ethyl, 2-(triphenylphosphonio)ethyl, isobutyl, vinyl, allyl, p-nitrophenyl, benzyl, p-methoxybenzyl, 3,4-dimethoxybenzyl, o-nitrobenzyl, p-nitrobenzyl, S-benzyl thiocarbonate, 4-ethoxy-1-naphthyl, methyl dithiocarbonate); groups with assisted cleavage (2-iodobenzoate, 4-azidobutyrate, 4-nitro-4-methylpentanoate, o-(dibromomethyl)benzoate, 2-formylbenzenesulfonate, 2-(methylthiomethoxy)ethyl carbonate, 4-(methylthiomethoxy)butyrate, miscellaneous esters (2,6-dichloro-4-methylphenoxyacetate, 2,6-dichloro-4-(1,1,3,3 tetramethylbutyl)phenoxyacetate, 2,4-bis(1,1-dimethylpropyl)phenoxyacetate, chlorodiphenylacetate, isobutyrate, monosuccinate, (E)-2-methyl-2-butenoate (tigloate), o-(methoxycarbonyl)benzoate, p-poly-benzoate, α-naphthoate, nitrate, alkyl N,N,N',N'-tetramethyl-phosphorodiamidate, n-phenylcarbamate, borate, 2,4-dinitrophenylsulfenate); and sulfonates (methanesulfonate (mesylate), benzenesulfonate, benzylsulfonate, tosylate, and triflate).

Compounds and Methods of the Invention

The invention provides novel compounds and methods for preparing various useful compounds, for example, compounds of formulas I-III. Certain specific compounds of the invention include, but are not limited to, 2-methyl-4-nitrobutanoic acid, 2-ethyl-4-nitrobutanoic acid, 2-(2-nitroethyl)pentanoic acid, 2-isopropyl-4-nitrobutanoic acid, 2-(2-nitroethyl)hexanoic acid, 4-nitro-2-phenylbutanoic acid, 2-benzyl-4-nitrobutanoic acid, 2,2-dimethyl-4-nitrobutanoic acid, 2,2-diethyl-4-nitrobutanoic acid, 2-ethyl-2-methyl-4-nitrobutanoic acid, 2-methyl-2-phenyl-4-nitrobutanoic acid, methyl 2-(2-ethyl-4-nitrobutanamido)-3-phenylpropanoate, methyl 2-(4-amino-2-ethylbutanamido)-3-phenylpropanoate, methyl 2-(4-(tert-butoxycarbonyl-amino)-2-ethylbutanamido)-3-phenylpropanoate, and various derivatives thereof, for example, the compounds of formulas I-III. Compounds that possess a chiral carbon can be prepared as either the (R)- or (S)-enantiomer. The derivatives include, for example, compounds where the alkyl or aryl group is substituted, and/or where the amine and/or acid moiety is protected.

The methods of the invention include preparing α-substituted-γ-nitrobutyraldehyde compounds. Nitroethylene and an aldehyde that has an α-hydrogen atom can be combined in the presence of an organic solvent, a proline derivative, and optionally a carboxylic acid under suitable reaction conditions to provide the α-substituted-γ-nitrobutyraldehyde. The proline derivative can be a chiral pyrrolidine catalyst, for example, an (S)- or (R)-diarylprolinol trialkyl silyl ether. The diarylprolinol trialkyl silyl ether can be a diphenylprolinol trialkyl silyl ether, such as (S)-diphenylprolinol trimethyl silyl ether or (R)-diphenylprolinol trimethyl silyl ether.

Depending on the substrates and catalyst employed, the catalyst can be present in varying amounts. Typically a higher catalyst loading is required in the absence of an acid co-catalyst. The proline derivative can be present, for example, in about 0.5 mol %, about 1 mol %, about 2 mol %, about 5 mol %, about 10 mol %, about 20 mol %, or about 50 mol %, with respect to the molar amount of nitroethylene.

When using a chiral catalyst, the reaction can provide the α-substituted-γ-nitrobutyraldehyde in enantiomerically enriched form. For example, products can have at least about 80% ee, at least about 90% ee, at least about 95% ee, at least about 98% ee, or at least about 99% ee. In addition to high enantiomeric purities, the reaction typically affords high yields, for example the yield of the α-substituted-γ-nitrobutyraldehyde is typically greater than about 80%. In several embodiments, the yield can be greater than about 50%, greater than about 70%, greater than about 80%, greater than about 90%, or greater than about 95% yield. Additionally, aldol products are typically afforded in less than about 20% yield, and are often observed in less than about 5%, or the aldol products are absent.

When the reaction includes an acid co-catalyst, a carboxylic acid often provides favorable results. The carboxylic acid can be acetic acid, trifluoroacetic acid, and the line, or a benzoic acid, and in some embodiments, an electron deficient benzoic acid. The carboxylic acid can be a nitrobenzoic acid, such as 3-nitrobenzoic acid. The acid can be present in any suitable and effective amount. For example, the acid cocatalyst can be present in about 1-200 mol % with respect to the molar amount of nitroethylene. Typically, about 2-100 mol %, or about 5-20 mol % of the cocatalyst is used. Standard amounts include multiples of 5 mol % ranging from 5-100 mol %, with respect to the molar amount of nitroethylene. In one specific embodiment, about 2 mol % of the chiral catalyst is used and about 5-20 mol % of the carboxylic acid is used, relative to the molar amount of nitroethylene.

Because of the reactive nature of nitroethylene, an excess of the aldehyde is often used in the reaction. Accordingly, in some embodiments the molar amount of the aldehyde is greater than the molar amount of nitroethylene. For example, the nitroethylene and the aldehyde can be present in anywhere from about a 1:1 molar ratio to about a 1:10 molar ratio. In some embodiments, the nitroethylene and the aldehyde are present in about a 1:2 molar ratio.

Any suitable and effective solvent can be used. Typical solvents include non-polar organic solvents such as alkanes and aryl solvents. Examples include but are not limited to hexanes, DMF, DMA, DMSO, benzene, toluene, and xylenes. In some instances, an acid can be used as the solvent. For example, the solvent can be a carboxylic acid, such as acetic acid, which can also act as a cocatalyst. When an acid is used as the solvent, other solvents may be optional and not required.

The reaction can typically be run at about 0° C., or 3° C., or up to about room temperature (~23° C.). Under some circumstances, it may be desirable to run the reaction at a low temperature, for example, at less than about 0° C., or about −30° C. to about 0° C. Under other circumstances, it may be desirable to heat the reaction to above room temperature, for example, to about 30° C., about 40° C., about 50° C., or to about the reflux temperature of the solvent used in the reaction. Increased reaction temperatures can increase the reaction rate or total conversion of the starting materials to the product.

The α-substituted-γ-nitrobutyraldehydes are excellent intermediates for the preparation of other valuable compounds, such as amino acids and related derivatives. Accordingly, the α-substituted-γ-nitrobutyraldehyde can be further manipulated, such as by reducing the aldehyde moiety of the α-substituted-γ-nitrobutyraldehyde to an alcohol, for example, using a borohydride reagent. The alcohol can then be oxidized to a carboxylic acid, for example, using an oxidizing agent such as a chromium reagent, for example, the Jones reagent.

Likewise, the nitro moiety of the α-substituted-γ-nitrobutyraldehyde can be to an amine, for example, using hydrogen gas and a transition metal reagent, such as palladium on carbon. Additionally, at any suitable point in the reaction sequence, a peptide bond can be formed with the carboxylic acid of the Michael adduct derivative, in combination with the nitrogen moiety of an amino acid, for example, one that has a protected carboxylic acid group. The invention further provides for the addition of protecting groups to the compounds prepared by the methods of the invention. For example, the amine group of the α-substituted-γ-amino acid can optionally be protected with a nitrogen protecting group.

The substituent of the aldehyde, such as the R groups of formulas I-IV, can be any organic group or functional group that is tolerant of the Michael addition reaction conditions. Examples include, but are not limited to, alkyl, cycloalkyl, aryl, heteroaryl, or heterocycle, wherein each group can be optionally substituted with one or more substituents.

Organocatalyzed Michael Addition Reactions

The invention provides a method to carry out an organocatalytic Michael addition of aldehydes to nitroethylene catalyzed by a pyrrolidine catalyst to provide β-substituted-δ-nitroalcohols. The reaction can be rendered enantioselective when a chiral pyrrolidine catalyst is used, resulting in Michael adducts in nearly optically pure form (e.g., 96-99% e.e.). The Michael adducts bear a single substituent adjacent to the carbonyl and can be efficiently converted to protected $\gamma^2$-amino acids, which are essential for systematic conformational studies of γ-peptide foldamers.

One method can be represented as illustrated in Scheme 3.

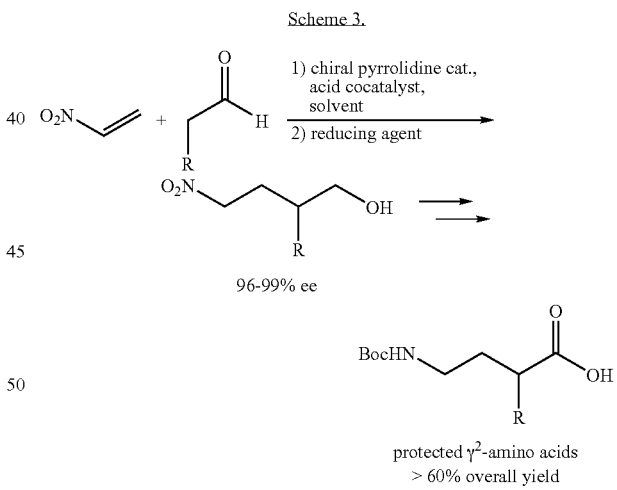

The chiral pyrrolidine catalyst can be, for example, proline or a diarylprolinol trialkyl silyl ether. The acid cocatalyst can be an organic acid such as acetic acid, trifluoroacetic acid, or a benzoic acid, for example, a nitrobenzoic acid. Suitable solvents include non-polar organic solvents such as hexanes, benzene, or toluene. The reducing agent can be, for example, a borohydride reagent such as sodium borohydride. The β-substituted-δ-nitroalcoholscan be provided in high yield and high enantiomeric excess. In place of the α-substituted aldehyde, and α,α-disubstituted aldehyde may be used to provide β,β-disubstituted-δ-nitro-aldehydes, alcohols, or acids.

The invention provides an asymmetric organocatalytic method for aminoethylation of aldehydes, which leads to a new and efficient synthesis of γ²-amino acids (Scheme 3). The novel approach pairs a chiral pyrrolidone catalyst with an acidic co-catalyst to promote Michael addition of aldehydes to nitroethylene with high enantioselectivity.

Catalyst Selection

Two chiral pyrrolidines, L-proline and (S)-diphenylprolinol trimethyl silyl ether (A), were evaluated for the ability to promote the Michael reaction between n-pentanal and nitroethylene (2:1 molar ratio).

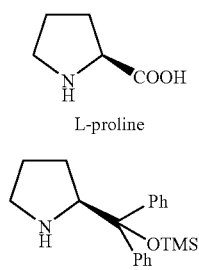

L-proline

A

Such reactions can in theory proceed via enamine intermediates. L-proline (20 mol %) provided very little of the Michael adduct. The major product in a variety of solvents was the product of the aldol condensation of n-pentanal, a process that is known to be catalyzed by proline.[11] In contrast, when 20 mol % A was employed in toluene, the desired Michael adduct was generated in 95% yield with >95% e.e., and little or no aldol product was formed. The enantiomeric excess of the product aldehyde was determined via an NMR-based assay.[12] The Michael adduct yield was somewhat lower in hexane, and the use of DMF or methanol provided reduced yields.

Co-Catalyst Selection

Previous work from Gellman and coworkers has shown that certain acidic co-catalysts can enhance pyrrolidine- or imidazolidinone-catalyzed Michael addition of aldehydes to enones,[13] therefore co-catalyst effects on the Michael addition of n-pentanal to nitroethylene was examined. When 5 mol % A was employed as catalyst, without any co-catalyst, <10% Michael adduct was generated after 1 hour, and little further adduct was generated after 24 hours (Table 1). However, use of 5 mol % A along with 200 mol % acetic acid (i.e., 2 equiv relative to nitroethylene) gave a 95% yield of the Michael adduct after 24 hours with excellent stereoselectivity (>95% e.e.). No apparent change of enantioselectivity was observed using the acidic co-catalysts. These observations suggest that the acidic component can facilitate catalyst turnover and/or prevent catalyst deactivation pathways.

Many pyrrolidine-catalyzed processes require relatively high levels of catalyst (10-20 mol %). The amounts of A and the co-catalyst that could be decreased while retaining a high extent of reaction were investigated (Table 1). Use of 2 mol % A with 20 mol % acetic acid led to a substantial decline in efficiency (30% Michael adduct). Switching to a more acidic co-catalyst, trifluoroacetic acid (20 mol %), caused a decrease in yield (8% Michael adduct) relative to acetic acid. Increasing the amount of acetic acid to 200 mol % led to only a modest improvement (55% Michael adduct) relative to 20 mol % acetic acid. Evaluation of a number of other potential acidic co-catalysts identified 3-nitrobenzoic acid (B) as suitably effective: combining 2 mol % pyrrolidine A with 5 mol % B provided the Michael adduct in 96% yield with >95% e.e. Reactions were typically performed on a 0.5 mmol scale at a 0.5 M concentration of nitroethylene using 2 equiv. of aldehyde.

TABLE 1

Organocatalyzed Michael Reaction

| entry | catalyst | co-catalyst | | yield[b] (%) | ee[c] |
|---|---|---|---|---|---|
| 1 | 20 mol % | none | | 95 | >95% |
| 2 | 5 mol % | none | | <10 | n.d.[d] |
| 3[a] | 5 mol % | HOAc | (200 mol %) | 95 | >95% |
| 4 | 2 mol % | HOAc | (20 mol %) | 30 | n.d.[d] |
| 5 | 2 mol % | TFA | (20 mol %) | 8 | n.d.[d] |
| 6[a] | 2 mol % | HOAc | (200 mol %) | 55 | n.d.[d] |
| 7 | 2 mol % | B | (5 mol %) | 96 | >95% |

[a]HOAc used as solvent.
[b]From ¹H NMR of the crude reaction mixture.
[c]Determined by a ¹H NMR ee assay.
[d]Not determined.

Reaction Scope

Having established A+B as an effective catalyst/co-catalyst pair for enantioselective Michael reaction of n-pentanal, the scope for the aldehyde substrate was investigated (Table 2). These reactions were carried out with 2 mol % A and 20 mol % B (relative to the limiting reagent, nitroethylene) at 3° C. Enantioselectivity was determined in most cases after reduction of the initial aldehyde product to the corresponding β-substituted-δ-nitrobutanol derivative. This approach enabled e.e. determination via HPLC because aldehyde reduction eliminates the possibility of epimerization. As initially observed for n-pentanal, a variety of aldehydes with hydrocarbon appendages give excellent yields and enantioselectivities. Branched substrates, such as the β-branched substrate 3-methylbutanal, were also suitable. Elevated temperature (23° C.) aided full conversion to the product (Table 2, entry 3).

Using γ-amino acids to construct biologically active foldamers[14] will require access to examples that bear appropriately protected functional groups in the side chain. Entries 9-11 of Table 2 show that the catalytic Michael addition method enables incorporation of side chains corresponding to those of glutamic acid, tyrosine, and lysine, into γ²-amino acid precursors, with excellent yields and enantioselectivities. All reactions were performed on a 1.0 nmol scale at a 0.5 M concentration of nitroethylene using 2 equivalents of aldehyde.

TABLE 2

Efficient and Enantioselective Michael Reaction of aldehydes with nitroethylene

| entry | product | R | time (h) | yield (%)[a] | ee (%)[b] |
|---|---|---|---|---|---|
| 1 | 2a | Me | 48 | 95 | 98 |
| 2 | 2b | Et | 48 | 96 | 98 |
| 3 | 2c[c,d] | i-Pr | 32 | 94 | 97 |
| 4 | 2d | n-Bu | 48 | 95 | 99 |
| 5 | 2e | i-Bu | 54 | 94 | >99 |
| 6 | 2f | Bn | 32 | 93 | 99 |
| 7 | 2g[c] | $CH_2$-c-Hex | 48 | 93 | >99 |
| 8 | 2h[c] | $CH_2$COOMe | 54 | 92 | 96 |
| 9 | 2i | $(CH_2)_2COO^tBu$ | 54 | 94 | 97 |
| 10 | 2j | 4-$O^tBuC_6H_4CH_2$ | 32 | 94 | 98 |
| 11 | 2k | $(CH_2)_4N(Boc)_2$ | 48 | 92 | 98 |

[a]Isolated yield.
[b]Determined by chiral HPLC analysis (Chiralcel OD-H).
[c]Determined by chiral HPLC analysis (Chiralcel OD-H) on the corresponding aldehyde.
[d]Reaction conducted at 23° C.

Formal Aminoethylation of Aldehydes

Compound 2b, prepared on a 10 mmol-scale reaction, was used to show that the β-substituted-δ-nitrobutanol derivatives generated via the Michael addition/reduction sequence could be converted in a straightforward manner to appropriately protected, enantioenriched $γ^2$-amino acids (Scheme 4). Jones oxidation of 2b provided the γ-nitro-α-alkylbutyric acid 3, which was then transformed to protected $γ^2$-amino acid 4 in an efficient one-pot operation involving nitro group reduction followed by Boc protection.

Scheme 4.

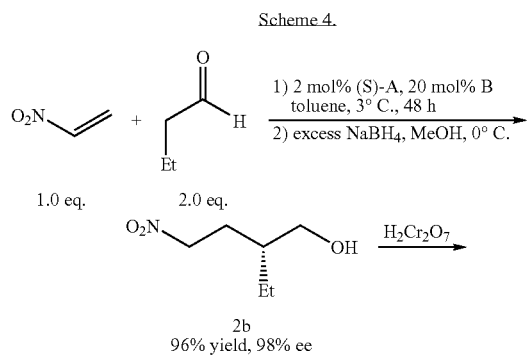

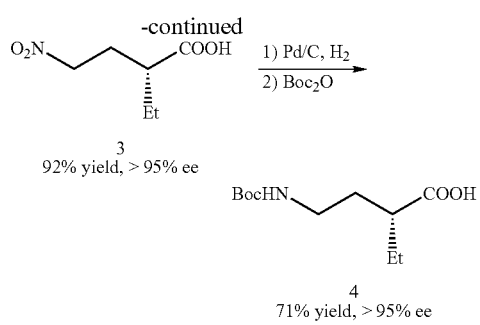

The absolute configuration of 2b was determined as (R) by X-ray structure analysis of the L-phenylalanine derivative 5 (Scheme 5), and other β-substituted-δ-nitrobutanol configurations were assigned by analogy. The enantiomeric excess of 3 and 4 was measured by NMR after coupling of these acids to L- and D-phenylalanine methyl ester. The short synthetic route in Scheme 4 provides a high overall yield (62% from nitroethylene) and is operationally simple. Thus, this approach offers access to multigram quantities of many $γ^2$-amino acids, including those with polar side chains.

Scheme 5.

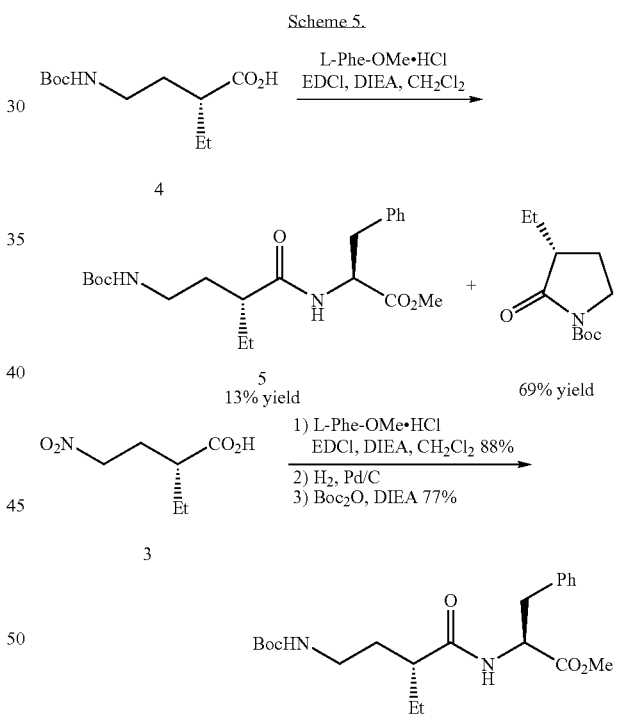

Incorporation of γ-amino acid residues into a growing peptide chain can be difficult because of cyclization side reactions. For example, carbodiimide-mediated coupling of Boc-protected $γ^2$-amino acid 4 (30 mM) to L-phenylalanine methyl ester provides only 13% yield of the desired amide; the major product under these conditions is the N-Boc γ-lactam derived from 4 (69%) (Scheme 5). However, the analogous reaction with γ-nitro acid 3, under identical conditions, gives the desired amide in 88% yield. The nitro group can be subsequently reduced via hydrogenation and protected. Thus, γ-nitro acids such as 3, important synthetic intermediates, are valuable building blocks for γ-peptide synthesis, with the nitro group serving as a protected amino group.

The highly enantioselective Michael additions described herein provide for the formal "aminoethylation" of aldehydes. The reaction can be catalyzed by a chiral pyrrolidine, and relatively low catalyst loading is possible, for example, when a carboxylic acid co-catalyst is used. When coupled with subsequent aldehyde reduction this process provides β-substituted-δ-nitrobutanol derivatives, which are potentially valuable chiral intermediates for organic synthesis. Such intermediates can be converted expeditiously to protected γ²-amino acids, which are important foldamer building blocks. Thus, a new and improved method for γ²-amino acid synthesis[10] is described herein, and the approach allows for diverse side chain functionality.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

General Materials and Instrumentation

Proton nuclear magnetic resonance (¹H NMR) spectra were recorded on Bruker AC-300 (300 MHz) spectrometers. Chemical shifts were recorded in parts per million (ppm, δ) relative to tetramethylsilane (δ0.00). ¹H NMR splitting patterns are designated as singlet (s), doublet (d), triplet (t), or quartet (q). All first-order splitting patterns were assigned on the basis of the appearance of the multiplet. Splitting patterns that could not be easily interpreted are designated as multiplet (m) or broad (br). Carbon nuclear magnetic resonance (¹³C NMR) spectra were recorded on a Bruker AC-300 (75 MHz) spectrometer. Mass spectra (MS) were obtained using an electrospray ionization (ESI) mass spectrometer.

Optical rotations were measured using a 1 mL cell with a 1 dm path length on a Perkin-Elmer 241 digital polarimeter and are reported as follows: $[\alpha]^{rt}_D$ (c in g per 100 mL solvent). Flasks were oven-dried overnight and cooled under a stream of nitrogen. All reagents were purchased from Aldrich Chemical Company. Flash chromatography was performed using silica gel 60 Å (32-63 mesh) from Sorbent Technologies. Reactions were monitored by thin layer chromatography (TLC) using 0.25 mm E. Merck pre-coated silica gel 60 (particle size 0.040-0.063 mm). Visualization was performed using a UV lamp or potassium permanganate stain.

Example 1

General Procedure for Organocatalytic Michael Reaction of Aldehydes with Nitroethylene To an 8 mL vial equipped with a small magnetic stir bar was added 1.2 mL dry toluene, an appropriate amount of amine catalyst (0.4 mL stock solution in toluene, [catalyst A]=0.05 M), 2.0 mmol (neat) aldehyde, and 0.2 mmol 3-nitrobenzoic acid (B) (33.4 mg). The mixture was stirred in an ice bath for about 5 minutes, and then 1 mmol nitroethylene (0.2 mL stock solution in toluene[nitroethylene]=0.05 M) was added. The total volume of the reaction mixture was about 2 mL ([nitroethylene] in reaction mixture ~0.5 M). The mixture was stirred in a cold room (3° C.). The reaction progress was monitored by ¹H NMR analysis of the crude reaction mixture.

Specifically, 50 μL crude reaction mixture was mixed with 600 μL DMSO-$d_6$ for ¹H NMR analysis. After the NMR showed that the reaction was complete, excess NaBH₄ (3.4 mmol, 128.5 mg) was added, followed by 10 mL MeOH, and the mixture was stirred for a few minutes. The mixture was then slowly poured into a 100 mL beaker containing 15 mL 1 M NH₄Cl at 0° C., the resulting mixture was extracted with EtOAc (about 3×10 mL). Extraction of the product into the organic phase was monitored by TLC analysis. The EtOAc layers were collected, washed with 20 mL brine, dried over MgSO₄ and filtered. The filtrate was concentrated to give the crude alcohol product, which was purified via SiO₂ column chromatography eluting with EtOAc/hexane to give the desired β-substituted-δ-nitroalcohols.

Aldehydes 2e and 2g were prepared in one step from commercially available alcohols via PCC oxidation. Aldehydes 2i-2k were each prepared in a few steps from commercially available materials; see: Gellman and coworkers, *J. Am. Chem. Soc.* 2007, 129, 6050.

Example 2

Coupling Boc-Protected γ-Amino Acid to L-Phe-OMe

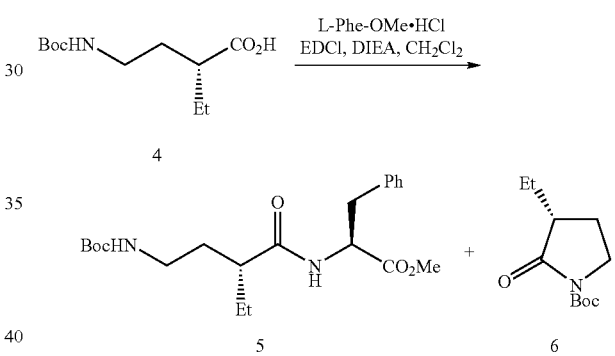

Compound 4 (139 mg, 0.6 mmol) was dissolved in dry dichloromethane (20 ml). Then L-Phe-OMe.HCl (142 mg, 0.66 mmol), EDCI.HCl (138 mg, 0.72 mmol) and DIEA (128 uL, 0.72 mmol) were successively added. The mixture was stirred 24 h at room temperature. The reaction mixture was acidified with aqueous NaHSO₄, extracted with EtOAc (3×). The organic layers were washed with saturated NaHCO₃ and brine. The combined organic layers were dried (MgSO₄), filtered and concentrated. The residue was purified via column chromatography eluting with EtOAc/hexane to give 5 as a while solid.

Example 3

Coupling γ-Nitro-α-Alkylbutyric Acid to L-Phe-OMe

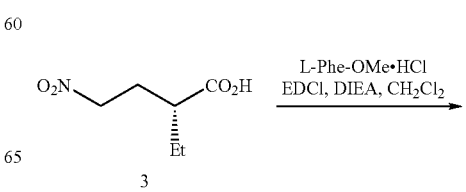

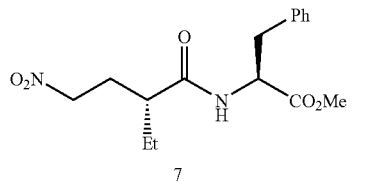

γ-Nitro-α-ethylbutyric acid 3 (97 mg, 0.6 mmol) was dissolved in dry dichloromethane (20 ml). Then L-Phe-OMe-·HCl (142 mg, 0.66 mmol), EDCI.HCl (138 mg, 0.72 mmol), DIEA (128 uL, 0.72 mmol) and catalytic amount of DMAP were successively added. The mixture was stirred 24 h at room temperature, then was acidified with aqueous NaHSO$_4$, extracted with EtOAc (3×). The organic layers were washed with saturated NaHCO$_3$ and brine. The combined organic layers were dried (MgSO$_4$), filtered and concentrated. The residue was purified via column chromatography eluted with EtOAc/hexane to give L-phenylalanine derivative 7 as a while solid.

| entry | coupling condition | yield (%) of 5, yield of lactam | yield (%) of 7[a] |
|---|---|---|---|
| 1 | 1.2 eq DIEA concentration = 0.1 M, rt | 80%, 6% | 90% |
| 2 | 1.2 eq DIEA concentration = 0.03 M, rt | 13%, 69% | 88% |
| 3 | 3.0 eq DIEA concentration = 0.1 M, rt | 15%, 67% | 70% |
| 4 | 1.2 eq DIEA concentration = 0.1 M, 35° C. | 76%, 8% | 87% |

[a]5-10% DMAP will accelerate the reaction

Example 4

Stereochemistry Determination

The absolute configuration of acid 4 was assigned by comparing the optical rotation data with literature (*J. Chem. Soc. Perkin Trans* 1: 1996, 7, 621). Optical rotation: $[\alpha]^{rt}_D$ −9.4 (c 0.54, CH$_2$Cl$_2$). Lit. $[\alpha]^{rt}_D$ −16 (c 0.42, CH$_2$Cl$_2$). The Optical rotations were measured using a 1 mL cell with a 1 dm path length on a Perkin-Elmer 241 digital polarimeter, which was calibrated by a standard known compound (L-proline purchased from Fluka, $[\alpha]^{rt}_D$=−85.0 (c 5.0, H$_2$O)), measured $[\alpha]^{rt}_D$=−83.1 (c 5.0, H$_2$O).

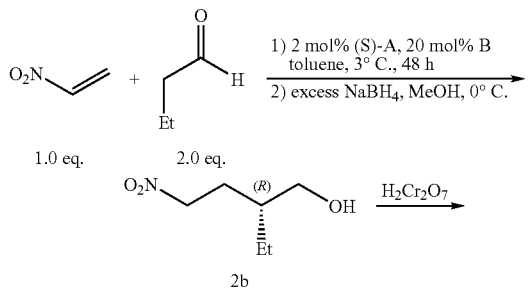

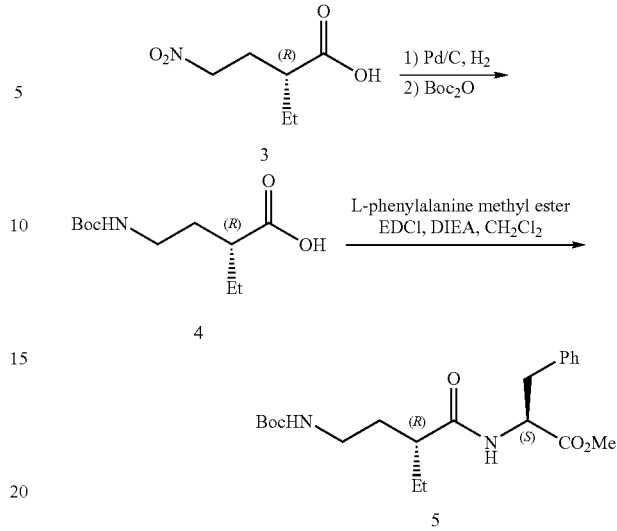

The absolute configuration of alcohol 2b from the Michael reaction/reduction sequence was assigned by the MPA model. See Latypov et al., *J. Org. Chem.* 1996, 61, 8569.

Synthesis of (R)-MPA Ester:

Compound 2b (17.3 mg, 0.118 mmol) was dissolved in dichloromethane (1.0 ml). Then (R)-2-methoxy-2-phenylacetic acid (MPA) (21.5 mg, 0.13 mmol), EDCI.HCl (25 mg, 0.13 mmol) and a catalytic amount of DMAP were successively added. The mixture was stirred 3.5 h at room temperature. Then the mixture was concentrated and purified via column chromatography eluting with EtOAc/hexane to give the (R)-MPA ester in quantitative yield.

$^1$H (CDCl3, 400 MHz) δ 7.45-7.31 (5H, m), 4.76 (1H, s), 4.28-4.14 (3H, m), 3.97-3.91 (1H, m), 3.41 (3H, s), 1.96-1.71 (2H, m), 1.66-1.54 (1H, m) 1.33-1.24 (2H, m), 0.87 (3H, t, J=7.5 Hz); $^{13}$C NMR (75 MHz, CDCl$_3$) δ 170.80, 136.41, 129.15, 128.97, 127.34, 82.67, 73.61, 66.48, 57.56, 36.68, 29.93, 11.09; HRMS m/z (ESI): calcd. for C$_{15}$H$_{21}$NO$_5$Na [M+Na]$^+$ 318.1312, found 318.1325.

Synthesis of (S)-MPTA Ester:

Compound 2b (13.8 mg, 0.094 mmol) was dissolved in dichloromethane (1.0 mL). Then (s)-2-methoxy-2-phenylacetic acid (MPA) (17.1 mg, 0.10 mmol), EDCI.HCl (19.8 mg, 0.10 mmol) and a catalytic amount of DMAP were successively added. The mixture was stirred 3.5 h at room temperature. Then the mixture was concentrated and purified via column chromatography eluting with EtOAc/hexane to give the (S)-MPA ester in quantitative yield. $^1$H (CDCl3, 300 MHz) δ 7.45-7.31 (5H, m), 4.76 (1H, s), 4.33-4.19 (2H, m), 4.12, 4.01 (AB of ABX, J$_{AB}$=11.3 Hz, J$_{AX}$=4.5 Hz, J$_{BX}$=6.6 Hz, 2H), 3.41 (3H, s), 2.01-1.78 (2H, m), 1.70-1.58 (1H, m), 1.30-1.19 (2H, m), 0.84 (3H, t, J=7.5 Hz).

Representation of MPA Ester with Δδ and Determination of Absolute Configuration According to Model (see *J. Org. Chem.* 1996, 61, 8569)

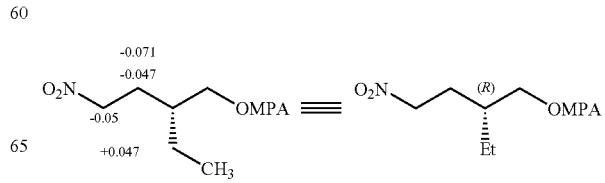

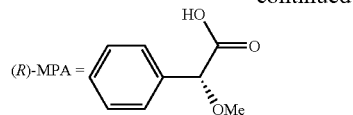

Δδ$^{R-S}$=δ((R)-MPA ester)−δ((S)-MPA ester)

The absolute configuration of compound 2b was determined by X-ray structure analysis of phenylalanine derivative 5.

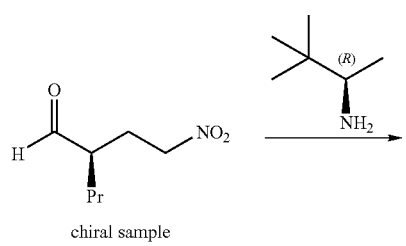

The absolute configuration of other β-substituted-δ-nitroalcohols from the Michael reaction/reduction sequence was assigned by analogy.

Example 5

Determination of the Michael Product ee Via $^1$H NMR Assay

Determination of the Michael product ee via $^1$H NMR assay was carried out by the methods described by Chi, Peelen, and Gellman, *Org. Lett.* 2005, 7, 3469. The racemic Michael product was prepared by using 20 mol % D,L-proline for the Michael reaction in toluene. D,L-Proline alone gave mostly the aldol product. 2-Diphenylmethyl-pyrrolidine (the mixture of (R) and (S), (R:S=1:1)) was used as a catalyst to prepare the racemic Michael product for HPLC. The chiral sample was prepared according to standard procedure II. All the Michael products used for ee determination described here were purified via silica gel column chromatography, but it should be noted that the crude reaction mixture may be used directly for ee determination in rapid screening of catalysts and reaction conditions.[5] In a typical procedure, 20 µL Michael product was dissolved in 650 µL DMSO-d$_6$ in an NMR tube, and 40 µL chiral primary amine was then added. The mixture was shaken for a few seconds, and the $^1$H NMR spectrum was obtained immediately. An example of the ee determination is illustrated below.

Determination of ee of a Michael Product by $^1$H NMR Assay chiral sample

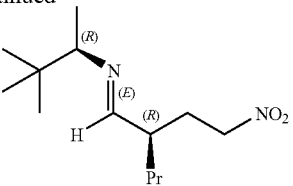

> 95% ee by the $^1$H NMR assay

Example 6

Nitroethylene

This compound was prepared using a modification of a literature procedure (see Kunetsky et al., *Tetrahedron Lett.* 2005, 46, 5203; Ranganathan et al, *Tetrahedron Lett.* 1987, 28, 2893). 2-Nitroethanol (100 g) and phthalic anhydride (210 g) were mixed in a 500 ml round bottom flask equipped with a magnetic stir bar. The flask was then equipped with a vacuum distillation setup with a fractional distillation column and a −78° C. bath-cooled receiver. The apparatus was evacuated to about 60 mm Hg, and the oil bath was heated to and maintained at 110-140° C. The starting materials turned to a homogeneous solution (solid material may exist depending on the temperature), and the distillate was collected until the distillation ceased to give a pale yellow solid at −78° C. The solid, containing a mixture of nitroethylene and water (~90 g, 90% yield), was warmed in an ice-water bath to give a pale yellow heterogeneous mixture. The mixture was mixed with toluene, dried over anhydrous CaCl$_2$ (anhydrous), and filtered through a pad of anhydrous CaCl$_2$. The filtrate was collected as a pale yellow stock solution of nitroethylene in toluene, and stored at −10° C. for future use.

The concentration of nitroethylene of the stock solution can be estimated via $^1$H NMR analysis in benzene-d6 (with toluene as internal standard). Concentration estimated from the $^1$H NMR analysis agreed with that calculated from mass of the crude nitroethylene product (the impurity is water) and toluene used in preparation of the stock solution. Nitroethylene as a solution in dry benzene was found to be stable (no change in NMR) for at least 6 months when stored in a refrigerator. $^1$H NMR of stock solution in toulene (300 MHz, CDCl$_3$) δ 7.11 (dd, J=7.2, 15 Hz), 6.62 (dd, J=14.7, 2.1 Hz), 5.86 (br d, J=7 Hz); $^{13}$C NMR of stock solution in toluene (75 MHz, CDCl$_3$) δ 145.56, 122.36.

Example 7

(R)-2-Methyl-4-nitrobutan-1-ol (2a)

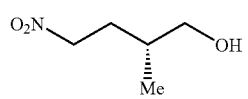

The product was obtained as a yellow oil following the standard procedure and purified by column chromatography. TLC R$_f$=0.38 (EtOAc/hexanes, v/v, 1:1). The enantiomeric excess was determined by HPLC using a Chiracel OD-H column, λ=220 nm, hexane/isopropanol (v/v:99/1, premixed), flow rate=0.4 mL/min; t$_R$=198.2 min (minor), 202.4 min (major) (98% ee); $^1$H NMR (300 MHz, CDCl$_3$) δ 4.57-

4.43 (m, 2H), 3.59, 3.50 (AB of ABX, $J_{AB}$=10.7 Hz, $J_{AX}$=5.3 Hz, $J_{BX}$=6.6 Hz, 2H), 2.27-2.15 (m, 1H), 1.96-1.84 (m, 1H), 1.82-1.71 (m, 1H), 1.58-1.57 (m, 1H), 0.98 (d, J=6.7 Hz, 3H); $^{13}$C NMR (75 MHz, CDCl$_3$) δ 74.24, 67.61, 33.31, 31.37, 16.44. HRMS m/z (ESI): calcd. for C$_5$H$_{11}$NO$_3$Na [M+Na]$^+$ 156.0637, found 156.0642. Optical rotation: $[\alpha]^{rt}_D$ +17.04 (c 1.08, CHCl$_3$).

Example 8

(R)-2-Ethyl-4-nitrobutan-1-ol 2b

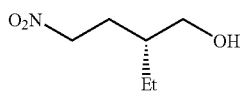

2b

The product was obtained as a yellow oil following the standard procedure and purified by column chromatography, TLC $R_f$=0.55 (EtOAc/hexanes, v/v, 1:1). The enantiomeric excess was determined by HPLC using a Chiracel OD-H column, λ=220 nm, hexane/isopropanol (v/v:98/2, premixed), flow rate=0.8 mL/min; $t_R$=61.45 min (minor), 66.08 min (major) (99% ee); $^1$H NMR (300 MHz, CDCl$_3$) δ 4.51 (t, J=7.4 Hz, 2H), 3.69-3.66 (m, 1H), 3.58-3.48 (m, 1H), 2.13-2.06 (m, 2H), 1.58-1.50 (m, 1H), 1.47 (m, 1H), 1.44-1.31 (m, 2H), 0.94 (t, J=7.5 Hz, 3H); $^{13}$C NMR (75 MHz, CDCl$_3$) δ 74.40, 64.94, 39.58, 29.43, 23.73, 11.33. HRMS m/z (ESI): Exact mass calcd. for C$_6$H$_{13}$NO$_3$Na [M+Na]$^+$ 170.0793, found 170.0795. Optical rotation: $[\alpha]^{rt}_D$ +1.06 (c 2.26, CHCl$_3$).

Example 9

(S)-3-Methyl-2-(2-nitroethyl)butanal 2c

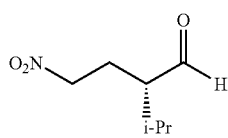

2c

The product was obtained as a yellow oil following the standard procedure without reduction and purified by column chromatography, TLC $R_f$=0.50 (EtOAc/hexanes, v/v, 1:3). The enantiomeric excess was determined by HPLC using a Chiracel OD-H column, λ=220 nm, hexane/isopropanol (v/v: 99.7/0.3, premixed), flow rate=1.0 mL/min; $t_R$=33.6 min (minor), 35.0 min (major) (97% ee); $^1$H NMR (300 MHz, DMSO-d$_6$) δ 9.61 (d, J=1.5 Hz, 1H), 4.61-4.41 (m, 2H), 2.36-2.29 (m, 1H), 2.23-2.07 (m, 2H), 2.03-1.92 (m, 1H), 0.94 (d, J=6.6 Hz, 3H), 0.89 (d, J=7.2 Hz, 3H); $^{13}$C NMR (75 MHz, DMSO-d$_6$) δ 205.50, 74.41, 54.26, 28.05, 22.68, 20.33, 19.54. HRMS m/z (ESI): Exact mass calcd. for C$_7$H$_{13}$NO$_3$Na [M+Na]$^+$ 182.0793, found 182.0786. Optical rotation: $[\alpha]^{rt}_D$ −11.34 (c 1.34, CHCl$_3$).

Example 10

(R)-2-(2-Nitroethyl)hexan-1-ol 2d

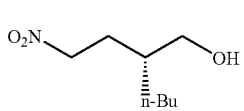

2d

The product was obtained as a yellow oil following the standard procedure and purified by column chromatography, TLC $R_f$=0.23 (EtOAc/hexanes, v/v, 1:3). The enantiomeric excess was determined by HPLC using a Chiracel OD-H column, λ=220 nm, hexane/isopropanol (v/v:99/1, premixed), flow rate=0.7 mL/min; $t_R$=84.7 min (minor), 87.7 min (major) (99% ee); $^1$H NMR (300 MHz, CDCl$_3$) δ 4.51 (t, J=7.4 Hz, 2H), 3.67, 3.53 (AB of ABX, $J_{AB}$=10.7 Hz, $J_{AX}$=4.3 Hz, $J_{BX}$=6.6 Hz, 2H), 2.13-2.06 (m, 2H), 1.64-1.56 (m, 2H), 1.31-1.30 (m, 6H), 0.90 (t, J=6.7 Hz, 3H); $^{13}$C NMR (75 MHz, CDCl$_3$) δ 74.39, 65.33, 38.06, 30.77, 29.82, 29.17, 23.05, 14.15. HRMS m/z (ESI): Exact mass calcd. for C$_8$H$_{17}$NO$_3$Na [M+Na]$^+$ 198.1106, found 198.1102. Optical rotation: $[\alpha]^{rt}_D$ +4.14 (c 1.16, CHCl$_3$).

Example 11

(R)-4-Methyl-2-(2-nitroethyl)pentan-1-ol 2e

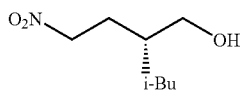

2e

The product was obtained as a yellow oil following the standard procedure and purified by column chromatography, TLC $R_f$=0.35 (EtOAc/hexanes, v/v, 1:3). The enantiomeric excess was determined by HPLC using a Chiracel OD-H column, λ=220 nm, hexane/isopropanol (v/v:99/1, premixed), flow rate=0.7 mL/min; $t_R$=72.7 min (minor), 76.9 (major) (>99% ee); $^1$H NMR (300 MHz, CDCl$_3$) δ 4.51 (t, J=7.5 Hz, 2H), 3.67, 3.53 (AB of ABX, $J_{AB}$=9.0 Hz, $J_{AX}$=0.7 Hz, $J_{BX}$=6.8 Hz, 2H), 2.12-2.05 (m, 2H), 1.75-1.57 (m, 2H), 1.36 (m, 1H), 1.28-1.19 (m, 1H), 1.15-1.06 (m, 1H), 0.90 (t, J=6.7 Hz, 6H); $^{13}$C NMR (75 MHz, CDCl$_3$) δ 74.32, 65.57, 40.56, 35.72, 25.47, 22.99, 22.85. HRMS m/z (ESI): Exact mass calcd. for C$_8$H$_{17}$NO$_3$Na [M+Na]$^+$ 198.1106, found 198.1098. Optical rotation: $[\alpha]^{rt}_D$ +1.28 (c 0.78, CHCl$_3$).

Example 12

(R)-2-Benzyl-4-nitrobutan-1-ol 2f

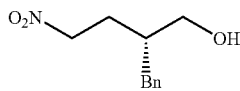

2f

The product was obtained as a yellow oil following the standard procedure and purified by column chromatography, TLC $R_f$=0.15 (EtOAc/hexanes, v/v, 1:3). The enantiomeric excess was determined by HPLC using a Chiracel OD-H column, λ=254 nm, hexane/isopropanol (v/v:95/5, premixed), flow rate=0.8 mL/min; $t_R$=41.3 min (minor), 44.6 min (major) (99% ee); $^1$H NMR (300 MHz, CDCl$_3$) δ 7.21 (m, 5H), 4.50-4.37 (t, J=7.4 Hz, 2H), 3.61, 3.49 (AB of ABX, $J_{AB}$=10.7 Hz, $J_{AX}$=4.0 Hz, $J_{BX}$=5.6 Hz, 2H), 2.69, 2.60 (AB of ABX, $J_{AB}$=13.7 Hz, $J_{AX}$=7.8 Hz, $J_{BX}$=6.9 Hz, 2H), 2.19-2.0 (m, 2H), 1.97-1.85 (m, 1H), 1.67 (s, 1H); $^{13}$C NMR (75 MHz, CDCl$_3$) δ139.50, 129.25, 128.84, 126.67, 74.28, 64.53, 39.95, 37.74, 29.51. HRMS m/z (ESI): Exact mass calcd. for $C_{11}H_{15}NO_3Na$ [M+Na]$^+$ 232.0950, found 232.0945. Optical rotation: $[\alpha]^{rt}_D$ −10.96 (c 0.912, CHCl$_3$).

Example 13

(R)-2-(Cyclohexylmethyl)-4-nitrobutanal 2g

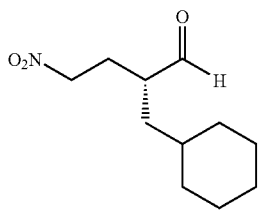

2g

The product was obtained as a yellow oil following the standard procedure without reduction and purified by flash column chromatography, TLC $R_f$=0.60 (EtOAc/hexanes, v/v, 1:3). The enantiomeric excess was determined by HPLC using a Chiracel OD-H column, λ=254 nm, hexane/isopropanol (v/v: 99.7/0.3, premixed), flow rate=1.0 mL/min; $t_R$=33.0 min (minor), 34.6 min (major) (>99% ee); $^1$H NMR (300 MHz, CDCl$_3$) δ 9.63 (d, J=0.9 Hz, 1H), 4.52-4.36 (m, 2H), 2.60-2.50 (m, 2H), 2.32-2.22 (m, 1H), 2.20-2.07 (m, 1H), 1.74-1.60 (m, 6H), 1.43-1.08 (m, 6H), 0.98-0.84 (m, 2H); $^{13}$C NMR (75 MHz, CDCl$_3$) δ 203.22, 73.41, 46.27, 36.72, 35.20, 33.65, 33.32, 26.52, 26.28, 26.25. HRMS m/z (ESI): Exact mass calcd. for $C_{11}H_{19}NO_3Na$ [M+Na]$^+$ 236.1263, found 236.1261. Optical rotation: $[\alpha]^{rt}_D$ +59.3 (c 1.345, CHCl$_3$).

Example 14

(S)-Methyl 3-formyl-5-nitropentanoate 2h

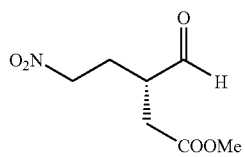

2h

The product was obtained as a yellow oil without reduction following the standard procedure and purified by flash column chromatography, TLC $R_f$=0.15 (EtOAc/hexanes, v/v, 1:3). The enantiomeric excess of the corresponding alcohol was determined by HPLC using a Chiracel OD-H column, λ=254 nm, hexane/isopropanol (v/v:90/10, premixed), flow rate=0.5 mL/min; $t_R$=36 min (minor), 38.7 (major) (96% ee); $^1$H NMR (300 MHz, CDCl$_3$) δ 9.74 (d, 1H), 4.58-4.43 (m, 2H), 3.72 (s, 3H), 2.94-2.85 (m, 1H), 2.78, 2.60 (AB of ABX, $J_{AB}$=16.8 Hz, $J_{AX}$=6.3 Hz, $J_{BX}$=6.0 Hz, 2H), 2.55-2.43 (m, 1H), 2.21-2.09 (m, 1H); $^{13}$C NMR (75 MHz, CDCl$_3$) δ 200.71, 171.45, 73.04, 52.47, 44.83, 33.28, 25.92. HRMS m/z (ESI): Exact mass calcd. for $C_7H_{11}NO_5$ [M+Na]$^+$ 212.0530, found 212.0528. Optical rotation: $[\alpha]^{rt}_D$ +9.9 (c 2.47, CHCl$_3$).

Example 15

(R)-tert-Butyl 4-(hydroxymethyl)-6-nitrohexanoate 2i

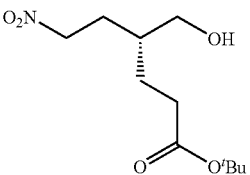

2i

The product was obtained as a yellow oil following the standard procedure and purified by column chromatography, TLC $R_f$=0.49 (EtOAc/hexanes, v/v, 1:1). The enantiomeric excess of the corresponding alcohol was determined by HPLC using a Chiracel OD-H column, λ=220 nm, hexane/isopropanol (v/v:95/5, premixed), flow rate=0.7 mL/min; $t_R$=26.9 min (minor), 28.9 (major) (97% ee) $^1$H NMR (300 MHz, CDCl$_3$) δ 4.57-4.44 (m, 2H), 3.65-3.57 (m, 2H), 2.39-2.21 (m, 2H), 2.16-2.01 (m, 2H), 1.96 (t, J=5.4 Hz, 1H), 1.74-1.56 (m, 3H), 1.45 (s, 9H); $^{13}$C NMR (75 MHz, CDCl$_3$) δ 168.66, 76.33, 69.32, 59.18, 33.04, 28.13, 24.84, 23.51, 20.82. HRMS m/z (ESI): calc. for $C_{11}H_{21}NO_5Na$ [M+Na]$^+$ 270.1312, found 270.1300. Optical rotation: $[\alpha]^{rt}_D$ −4.60 (c 1.24, CHCl$_3$).

Example 16

(R)-2-(4-tert-butoxybenzyl)-4-nitrobutan-1-ol 2j

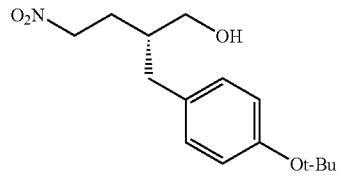

2j

The product was obtained as a yellow oil following the standard procedure and purified by column chromatography, TLC $R_f$=0.55 (EtOAc/hexanes, v/v, 1:1). The enantiomeric excess of the corresponding alcohol was determined by HPLC using a Chiracel OD-H column, λ=220 nm, hexane/isopropanol (v/v:95/5, premixed), flow rate=1.0 mL/min; $t_R$=27.3 min (minor), 30.3 (major) (98% ee); $^1$H NMR (300 MHz, CDCl$_3$) δ 7.04 (d, J=8.3 Hz, 2H), 6.91 (d, J=8.3 Hz, 2H), 4.49-4.32 (m, 2H), 3.61, 3.49 (AB of ABX, $J_{AB}$=10.4 Hz, $J_{AX}$=4.5 Hz, $J_{BX}$=5.8 Hz, 2H), 2.65, 2.56 (AB of ABX, $J_{AB}$=13.7 Hz, $J_{AX}$=7.8 Hz, $J_{BX}$=7.1 Hz, 2H), 2.19-1.99 (m, 2H), 1.94-1.81 (m, 1H), 1.59 (bs, 1H), 1.33 (s, 9H); $^{13}$C NMR (75 MHz, CDCl$_3$) δ 154.02, 134.33, 129.57, 124.53, 78.64, 74.28, 64.58, 40.01, 37.08, 29.54, 29.03. HRMS m/z (ESI): calc. for $C_{15}H_{23}NO_4Na$ [M+Na]$^+$ 304.1525, found 304.1521. Optical rotation: $[\alpha]^{rt}_D$ −5.28 (c 1.42, CHCl$_3$).

Example 17

Boc-Protected 2k

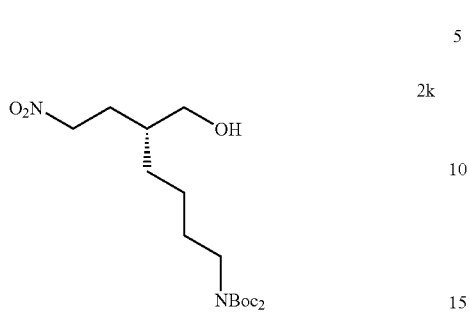

The product was obtained as a yellow oil following the standard procedure and purified by column chromatography, TLC $R_f$=0.15 (EtOAc/hexanes, v/v, 1:3). The enantiomeric excess of the corresponding alcohol was determined by HPLC using a Chiracel OD-H column, λ=220 nm, hexane/isopropanol (v/v:98/2, premixed), flow rate=0.35 mL/min; $t_R$=97.9 min (minor), 100.6 (major) (98% ee); $^1$H NMR (300 MHz, CDCl$_3$) δ 4.53-4.48 (m, 2H), 3.67-3.52 (m, 4H), 2.12-2.05 (m, 2H), 1.62-1.56 (m, 5H), 1.51 (s, 18H), 1.40-1.30 (m, 3H); $^{13}$C NMR (75 MHz, CDCl$_3$) δ 153.19, 82.50, 74.29, 64.65, 45.98, 38.02, 30.43, 29.79, 29.22, 28.30, 23.90. HRMS m/z (ESI): calc. for C$_{18}$H$_{34}$N$_2$O$_7$Na [M+Na]$^+$ 413.2255, found 413.2273. Optical rotation: $[\alpha]^{rt}_D$ +1.70 (c 1.18, CHCl$_3$).

Example 18

γ$^2$-Amino Acid Synthesis

Briefly, butyraldehyde was subjected to the stereoselective Michael reaction conditions to afford β-substituted-δ-nitrobutyralcohol 2b. Jones oxidation of 2b provided the γ-nitro-α-alkylbutyric acid 3, which was then transformed to protected γ$^2$-amino acid 4 in an efficient one-pot operation involving nitro group reduction followed by Boc protection.

Synthesis of α-Substituted-γ-Amino Acid

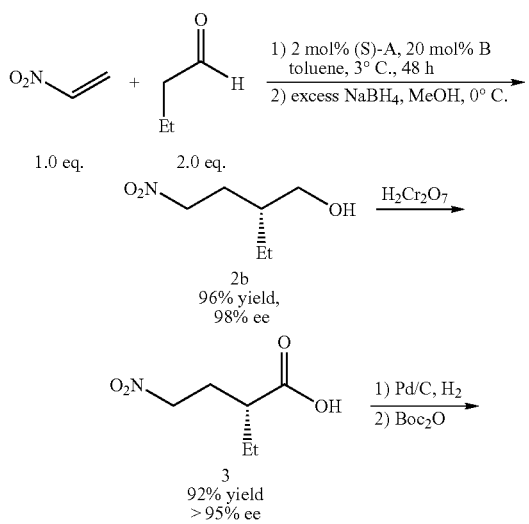

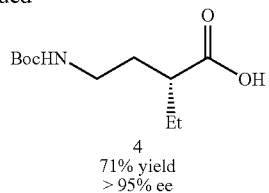

4
71% yield
>95% ee

Example 19

(R)-2-Ethyl-4-nitrobutanoic Acid 3

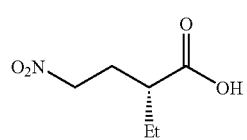

To 1.0 mmol alcohol 2b dissolved in 10 mL acetone at 0° C. was added 1.5 mmol H$_2$Cr$_2$O$_7$ (3 mL Jones reagent). The mixture was stirred for 5 h, during which time the mixture warmed to room temperature. Excess isopropanol was added, and the mixture was stirred for 10 min. The mixture was filtered, and the solution was diluted with 2 mL 2 N HCl and extracted with Et$_2$O. Complete extraction of the product into the Et$_2$O phase was monitored by TLC. The organic layers was washed with saturated NaCl, dried over MgSO$_4$, filtered and concentrated to give a viscous oil, of which the desired product 3 was purified via column chromatography eluting with EtOAc/hexane (1:10 to 1:3; v/v) to give pure product as a yellow oil in 92% yield. TLC $R_f$=0.45 (EtOAc/hexanes, v/v, 1:1) $^1$H NMR (300 MHz, CDCl$_3$) 4.56-4.41 (m, 2H), 2.53-2.44 (m, 1H), 2.38-2.19 (m, 2H), 1.84-1.60 (m, 2H), 1.00 (t, J=7.4 Hz, 3H); $^{13}$C NMR (75 MHz, CDCl$_3$) δ 180.66, 73.55, 43.57, 28.41, 25.24, 11.41. HRMS m/z (ESI): calc. for C$_6$H$_{11}$NO$_4$Na [M+Na]$^+$ 184.0586, found 184.0578. Optical rotation: $[\alpha]^{rt}_D$ +17.51 (c=3.82, CHCl$_3$). The ee of this compound (>95%) was determined by coupling one portion to L-Phe-OMe and another portion to D-Phe-OMe and then analyzing the products by $^1$H NMR spectroscopy.

Example 20

(R)-4-(tert-Butoxycarbonyl)-2-ethylbutanoic Acid 4

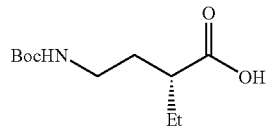

A mixture of nitro acid 3 (0.36 g, 2.2 mmol), ammonium formate (0.70 g, 11 mmol) and 10% Pd/C (dry, 0.21 g) in anhydrous MeOH (10 ml) was refluxed overnight under N$_2$ until the starting material disappeared as indicated by TLC analysis. The mixture was cooled to room temperature and filtered through a pad of celite. The filtrate was collected and concentrated to give the crude amine, which was dissolved in 10 ml CH$_2$Cl$_2$. DIEA (0.6 ml, 3.3 mmol) and Boc$_2$O (0.73 g, 3.3 mmol) were then added. The mixture was stirred at room temperature for 2 hours and concentrated to give a crude product, from which the desired Boc-protected γ²-amino acid 4 was isolated as an oil (71% yield) via column chromatography eluting with EtOAc/hexane.

$^1$H NMR (500 MHz, CDCl$_3$) (the broadness of the peaks and the presence of two NH peaks suggested that two interconverting rotamers were present) δ 10.81 (br s, 1H), 6.11 (br s, 0.30H), 4.74 (br s, 0.69H), 3.22-3.13 (m, 2H), 1.89-1.80 (m, 1H), 1.72-1.65 (m, 2H), 1.59-1.53 (m, 1H), 1.44 (s, 9H), 0.95 (t, J=7.0 Hz, 3H); $^{13}$C NMR (75 MHz, CDCl$_3$) δ 180.88, (176.58), 156.38, (158.04), (80.87), 79.51, (50.26), 44.63, (39.99), 38.83, 31.94, 28.49, 25.33, (20.98), 11.73 mixtures of rotamers; HRMS m/z (ESI): calc. for C$_{11}$H$_{21}$NO$_4$Na [M+Na]$^+$ 254.1368, found 254.1360. Optical rotation: [α]$^{rt}_D$ −9.4 (c 0.54, CH$_2$Cl$_2$). Lit. [α]$^{rt}_D$ −16 (c 0.42, CH$_2$Cl$_2$) The ee of this compound (>95%) was determined by coupling one portion to L-Phe-OMe and another portion to D-Phe-OMe and then analyzing the products by $^1$H NMR spectroscopy.

Example 21

(S)-Methyl 2-((R)-4-(tert-butoxycarbonyl)-2-ethylbutanamido)-3-phenylpropanoate 5

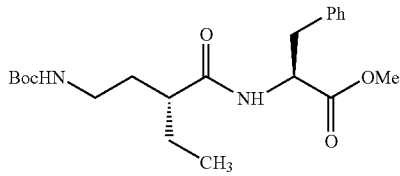

Compound 4 (139 mg, 0.6 mmol) was dissolved in dry CH$_2$Cl$_2$ (6 mL) and treated with L-Phe-OMe.HCl (142 mg, 0.66 mmol), EDCI.HCl (138 mg, 0.72 mmol), DIEA (128 uL, 0.72 mmol). The reaction mixture was stirred for 24 h, diluted with EtOAc, acidified with 10% citric acid and extracted with EtOAc (3×). The combined organic layers were washed with saturated NaHCO$_3$ and brine, dried (MgSO$_4$) and concentrated. The crude residue was purified via column chromatography eluting with EtOAc/hexane to afford pure product 5 (188 mg, 80%) as a white solid. An analytical sample was purified by recrystallization (hexanes/EtOAc): m.p. 119.5-121° C. TLC R$_f$=0.60 (EtOAc/hexanes, v/v, 1:1). $^1$H NMR (500 MHz, CDCl$_3$) δ 7.32-7.23 (m, 3H), 7.17-7.15 (m, 2H), 6.36 (bd, J=6.6 Hz, 1H), 4.96-4.89 (m, 1H), 4.54 (bs, 1H), 3.72 (s, 3H), 3.18, 3.07 (AB of ABX, J$_{AB}$=13.9 Hz, J$_{AX}$=6.0 Hz, J$_{BX}$=7.2 Hz, 2H), 3.00-2.84 (m, 2H), 2.08-1.98 (m, 1H), 1.73-1.49 (m, 3H), 1.44 (s, 9H), 1.47-1.36 (m, 1H), 0.85 (t, J=7.5 Hz, 3H); $^{13}$C NMR (75 MHz, CDCl$_3$) δ 175.23, 172.47, 156.43, 136.40, 129.38, 128.79, 127.28, 79.42, 53.16, 52.46, 46.46, 38.72, 38.18, 33.16, 28.61, 26.21, 12.04; HRMS m/z (ESI): calc. for C$_{21}$H$_{32}$N$_2$O$_5$Na [M+Na]$^+$ 415.2204, found 415.2199. Optical rotation: [α]$^{rt}_D$ +14.9 (c 1.06, CHCl$_3$). In addition, N-Boc γ-lactam (7.6 mg, 6%) was isolated via column chromatography eluting with EtOAc/hexane.

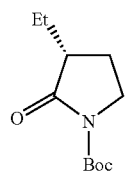

(R)-tert-Butyl 3-ethyl-2-oxopyrrolidine-1-carboxylate 6 colorless oil TLC R$_f$=0.40 (EtOAc/hexanes, v/v, 1:1). $^1$H NMR (300 MHz, CDCl$_3$) δ 3.80-3.72 (m, 1H), 3.62-3.53 (m, 1H), 2.49-2.38 (m, 1H), 2.21-2.11 (m, 1H), 1.98-1.85 (m, 1H), 1.74-1.59 (m, 1H), 1.53 (s, 9H), 1.51-1.39 (m, 1H), 0.98 (t, J=7.5 Hz, 3H); $^{13}$C NMR (75 MHz, CDCl$_3$) δ 176.13, 150.69, 82.87, 45.34, 44.68, 28.25, 23.88, 23.72, 11.63; HRMS m/z (ESI): calc. for C$_{11}$H$_{19}$NO$_3$H [M+H]$^+$ 214.1438, found 214.1447.

Example 22

(S)-Methyl 2-((R)-2-ethyl-4-nitrobutanamido)-3-phenylpropanoate 7

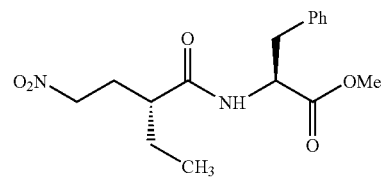

Nitro acid 3 (0.483 g, 3 mmol) was dissolved in dry CH$_2$Cl$_2$ (30 mL) and treated with L-Ph-OMe.HCl (0.78 g, 3.6 mmol), EDCI (0.69 g, 3.6 mmol), DIEA (0.64 mL, 3.6 mmol) and catalytic amount of DMAP. The reaction mixture was stirred for 24 h, diluted with EtOAc, acidified with 10% citric acid and extracted with EtOAc (3×). The combined organic layers were washed with saturated NaHCO$_3$ and brine, dried (MgSO$_4$) and concentrated. The crude residue was purified by chromatography (hexanes/EtOAc, v/v, 8:1 to 2:1) to afford pure product 7 (0.87 g, 90%) as a white solid. An analytical sample was purified by recrystallization (hexanes/EtOAc): m.p. 86.2-87.8° C., TLC R$_f$=0.66 (EtOAc/hexanes, v/v, 1:1), $^1$H NMR (300 MHz, CDCl$_3$) δ 7.34-7.22 (m, 3H), 7.17-7.14 (m, 2H), 6.12 (bd, J=8.1 Hz, 1H), 4.99 (dt, J=5.1, 8.0 Hz, 1H), 4.22-4.14 (m, 1H), 4.00-3.90 (m, 1H), 3.76 (s, 3H), 3.23, 2.98 (AB of ABX, J$_{AB}$=14.0 Hz, J$_{AX}$=5.2 Hz, J$_{BX}$=7.9 Hz, 2H), 2.17-2.01 (m, 3H), 1.70-1.56 (m, 1H), 1.52-1.38 (m, 1H), 0.89 (t, J=7.5 Hz, 3H); $^{13}$C NMR (75 MHz, CDCl$_3$) δ 173.61, 172.23, 136.09, 129.40, 128.92, 127.46, 73.54, 52.98, 52.67, 45.70, 38.32, 29.77, 26.20, 11.79; HRMS m/z (ESI): calc. for C$_{16}$H$_{22}$N$_2$O$_5$H [M+H]$^+$ 323.1602, found 323.1609. Optical rotation: [α]$^{rt}_D$ +14.3 (c 1.23, CHCl$_3$).

CITED DOCUMENTS (1) Perlmutter, P. *Conjugate Addition Reactions in Organic Synthesis*; Pergamon Press: Oxford, 1992.
(2) For general reviews on the asymmetric Michael reactions, see Jarvo, E. R.; Miller, S. J. *Tetrahedron* 2002, 58, 2481.
(3) For reviews, see Santanu, M.; Yang, J. W.; Hoffmann, S.; List, B. *Chem. Rev.* 2007, 107, 5471.
(4) For organocatalytic Michael reactions of aldehydes to nitroalkenes, see: (a) *Org. Lett.* 2001, 3, 3737. (b) *Org. Lett.* 2004, 6, 2527. (c) *J. Am. Chem. Soc.* 2006, 128, 4966. (d) O. *Org. Lett.* 2002, 4, 3611. (e) *Eur. J. Org. Chem.* 2004, 1577. (f) *Angew. Chem., Int. Ed.* 2005, 44, 1369. (g) *Angew., Chem. Int. Ed.* 2005, 44, 4212. (h) *Angew. Chem., Int. Ed.* 2005, 45, 6366. (i) *Org. Lett.* 2006, 8, 2559. (j) *Angew. Chem., Int. Ed.* 2006, 45, 5984.
(5) For organocatalytic Michael additions of non-aldehyde carbonyl nucleophiles to nitroalkenes, see: (a) *Chem. Commun.* 2006, 460. (b) *Org. Biomol. Chem.* 2006, 4, 63.

(6) Seebach, D.; Brenner, M.; Rueping, M.; Jaun, B. *Chem. Eur. J.* 2002, 8, 573.
(7) (a) *J. Org. Chem.* 2007, 72, 636. (b) *J. Am. Chem. Soc.* 2007, 129, 4039.
(8) For selected reviews, see: (a) *GABA in Nervous System Function the View at Fifty Years*; Martin, D. L.; Olson, R. W.; Ed.; Lippincott Williams & Williams & Wilkins: Philadelphia, Pa., 2000 (b) Bryans, J. S.; Wustrow, D. J. *Med. Res. Rev.* 1999, 19, 149. (c) Otsuka, M. *GABA: Receptors, Transporters and Metabolism* 1996, 1. (d) DeFeudis, F. V. *Annual review of pharmacology* 1975, 15, 105.
(9) For selected references of Pregabalin, see: (a) *J. Org. Chem.* 2007, 72, 7390. (b) *J. Am. Chem. Soc.* 2007, 129, 9216. For selected references of Baclofen, see: (c) Corey, E. J.; Zhang, F.-Y.; *Org. Lett.* 2000, 2, 4257. (d) Evans, D. A; Mito, S.; Seidel, D. *J. Am. Chem. Soc.* 2007, 129, 11583. (e) Gotoh, H.; Ishikawa, H.; Hayashi, Y. *Org. Lett.* 2007, 9, 5307.
(10) For recent review on synthesis of γ-amino acids, see: Ordóñez, M.; Cativiela, C. *Tetrahedron: Asymmetry* 2007, 18, 3. For selected synthesis examples, see: (a) Evans, D. A.; Gage, J. R.; Leighton, J. L.; Kim, A. S. *J. Org. Chem.* 1992, 57, 1961. (b) Azam, S.; D'Souza, A. A; Wyatt, P. B. *J. Chem. Soc., Perkin Trans.* 1 1996, 621. (c) Brenner, M.; Seebach, D. *Helv. Chim. Acta.* 1999, 82, 2365. (d) Camps, P.; Munoz-Torrero, D.; Sanchez, L. *Tetrahedron: Asymmetry* 2004, 15, 2039.
(11) (a) Córdova, A; Notz, W.; Barbas, C. F., III. *J. Org. Chem.* 2002, 67, 301. (b) Northrup, A. B.; MacMillan, D. W. C. *J. Am. Chem. Soc.* 2002, 124, 6798. (c) List, B. *Tetrahedron* 2002, 58, 5573.
(12) Chi, Y.; Peelen, T. J.; Gellman, S. H. *Org. Lett.* 2005, 7, 3469.
(13) (a) Peelen, T. J.; Chi, Y.; Gellman, S. H. *J. Am. Chem. Soc.* 2005, 127, 11598. (b) Chi, Y. G.; Gellman, S. H. Org. Len. 2005, 7, 4253. (c) Melchiorre, P.; Jorgensen, K. A. *J. Org. Chem.* 2003, 68, 4151.
(14) (a) *Nat. Chem. Biol.* 2007, 3, 252. (b) *Angew. Chem., Int. Ed.* 2003, 42, 776.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method for preparing an α-substituted-γ-nitrobutyraldehyde comprising contacting nitroethylene and an aldehyde that has at least one α-hydrogen, in the presence of an organic solvent, a proline derivative, and a carboxylic acid, for a period of time sufficient to provide the α-substituted-γ-nitrobutyraldehyde; wherein the beta-carbon of the α-substituted-γ-nitrobutyraldehyde is a methylene, and aldol products are afforded in less than about 20% yield with respect to the molar amount of nitroethylene.

2. The method of claim 1 wherein the aldehyde has an α-methylene group or an α-methine group.

3. The method of claim 1 wherein the proline derivative is a chiral pyrrolidine catalyst and the α-substituted-γ-nitrobutyraldehyde is prepared in at least about 80% enantiomeric purity.

4. The method of claim 3 wherein the chiral pyrrolidine catalyst is an (S)- or (R)-diphenylprolinol trialkyl silyl ether.

5. The method of claim 4 wherein about 1-10 mol % of the chiral pyrrolidine catalyst is present with respect to the molar amount of nitroethylene, wherein the carboxylic acid is optionally acetic acid or a nitrobenzoic acid, and the organic solvent is optionally an aryl solvent.

6. The method of claim 5 wherein the carboxylic acid is present in about 5-20 mol % with respect to the molar amount of nitroethylene.

7. The method of claim 1 wherein the molar amount of the aldehyde is greater than the molar amount of nitroethylene.

8. The method of claim 1 further comprising reducing the aldehyde moiety of the α-substituted-γ-nitrobutyraldehyde to an alcohol, and optionally oxidizing the alcohol to a carboxylic acid, and optionally reducing the nitro moiety to an amine.

9. A method for preparing a compound of formula III:

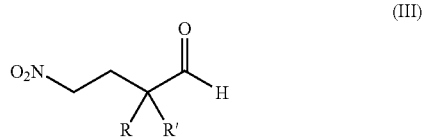

(III)

wherein R and R' are each independently hydrogen or optionally substituted alkyl, cycloalkyl, aryl, heteroaryl, or heterocycle;
comprising contacting a compound of formula IV:

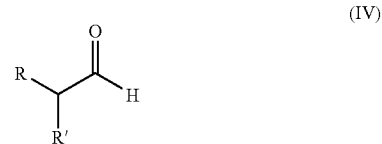

(IV)

wherein R and R' are as defined for formula III, and nitroethylene, in the presence of an organic solvent, a proline derivative, and a carboxylic acid, for a period of time sufficient to provide the compound of formula III; wherein aldol products are afforded in less than about 20% yield with respect to the molar amount of nitroethylene.

10. The method of claim 9 wherein the proline derivative is a chiral pyrrolidine catalyst and the compound of formula III is prepared in an enantiomerically enriched form.

11. A method for preparing a α-substituted-γ-nitrobutyraldehyde comprising contacting nitroethylene and an aldehyde that has an α-methylene group, in the presence of an organic solvent, an (S)- or (R)-diphenylprolinol trialkyl silyl ether, and a carboxylic acid;
for a period of time sufficient to provide the α-substituted-γ-nitrobutyraldehyde, wherein the beta-carbon of the α-substituted-γ-nitrobutyraldehyde is a methylene, aldol products are afforded in less than about 20% yield with respect to the molar amount of nitroethylene, and the α-substituted-γ-nitrobutyraldehyde is prepared in at least about 90% enantiomeric purity.

12. The method of claim 3 wherein the chiral pyrrolidine catalyst is (S)-diphenylprolinol trimethyl silyl ether or (R)-diphenylprolinol trimethyl silyl ether.

13. The method of claim 12 wherein the α-substituted-γ-nitrobutyraldehyde has an enantiomeric purity of greater than about 95%.

14. The method of claim 10 wherein the chiral pyrrolidine catalyst is (S)-diphenylprolinol trimethyl silyl ether or (R)-diphenylprolinol trimethyl silyl ether.

15. The method of claim 14 wherein the compound of formula III has an enantiomeric purity of greater than about 95%.

16. The method of claim 11 further comprising reducing the aldehyde of the α-substituted-γ-nitrobutyraldehyde to an alcohol, and optionally oxidizing the alcohol to a carboxylic acid.

17. The method of claim 1 wherein the carboxylic acid is acetic acid or a nitrobenzoic acid, and the organic solvent is the carboxylic acid or an aryl solvent.

18. The method of claim 5 wherein the carboxylic acid is acetic acid or a nitrobenzoic acid, and the organic solvent is the carboxylic acid or an aryl solvent.

19. The method of claim 11 wherein the carboxylic acid is present in about 5-20 mol % with respect to the molar amount of nitroethylene.

20. The method of claim 1 wherein the carboxylic acid is 3-nitrobenzoic acid.

21. The method of claim 9 wherein the carboxylic acid is 3-nitrobenzoic acid.

22. The method of claim 11 wherein the carboxylic acid is 3-nitrobenzoic acid.

* * * * *

UNITED STATES PATENT AND TRADEMARK OFFICE
CERTIFICATE OF CORRECTION

| | | |
|---|---|---|
| PATENT NO. | : 8,269,039 B2 | |
| APPLICATION NO. | : 12/383370 | |
| DATED | : September 18, 2012 | |
| INVENTOR(S) | : Gellman et al. | |

It is certified that error appears in the above-identified patent and that said Letters Patent is hereby corrected as shown below:

In the Specification

Please delete the federal grant/funding clause at column 1 lines 12-16 and substitute therefor:

--This invention was made with government support under GM056414 awarded by the

National Institutes of Health and 0140621 and 0551920 awarded by the National Science Foundation.

The government has certain rights in the invention.--

Signed and Sealed this
Thirteenth Day of May, 2014

Michelle K. Lee
*Deputy Director of the United States Patent and Trademark Office*